(12) United States Patent
Sacks et al.

(10) Patent No.: US 12,564,517 B2
(45) Date of Patent: Mar. 3, 2026

(54) AVOIDING BLOOD VESSELS DURING DIRECT SELECTIVE LASER TRABECULOPLASTY

(71) Applicant: BELKIN VISION LTD., Yavne (IL)

(72) Inventors: Zachary Sacks, Modiin (IL); Daria Lemann-Blumenthal, Bitzaron (IL); Daniel Elkayam, Rehovot (IL); Masha Dobkin-Bekman, Rishon Lezion (IL); Yoram Solberg, Herzliya (IL); Eli Makdasi, Rehovot (IL); Sergey Volfson, Nes Ziona (IL)

(73) Assignee: Belvin Vision Ltd., Yavne (IL)

( * ) Notice: Subject to any disclaimer, the term of this patent is extended or adjusted under 35 U.S.C. 154(b) by 379 days.

(21) Appl. No.: 18/025,923

(22) PCT Filed: Oct. 25, 2021

(86) PCT No.: PCT/IB2021/059821
§ 371 (c)(1),
(2) Date: Mar. 13, 2023

(87) PCT Pub. No.: WO2022/090894
PCT Pub. Date: May 5, 2022

(65) Prior Publication Data
US 2023/0329911 A1     Oct. 19, 2023

Related U.S. Application Data

(63) Continuation-in-part of application No. 17/136,052, filed on Dec. 29, 2020, now Pat. No. 12,109,149.
(Continued)

(51) Int. Cl.
*A61F 9/008* (2006.01)

(52) U.S. Cl.
CPC ..................... *A61F 9/00821* (2013.01); *A61F 2009/00868* (2013.01); *A61F 2009/00891* (2013.01)

(58) Field of Classification Search
None
See application file for complete search history.

(56) References Cited

U.S. PATENT DOCUMENTS 2,635,502 A     4/1953   Richards
3,594,072 A     7/1971   Feather
(Continued)

FOREIGN PATENT DOCUMENTS

AU     2011379044 B2     4/2013
AU     2015210430 A1     9/2015
(Continued)

OTHER PUBLICATIONS

Rashad, "What is the EASIEST Way to do YAG Laser Posterior Capsulotomy?", YouTube Clip, p. 1, Jul. 17, 2020 https://www.youtube.com/watch?v=g0pV3UGo_2o.
(Continued)

*Primary Examiner* — Michael T. Holtzclaw
(74) *Attorney, Agent, or Firm* — Meitar Patents LTD.; Daniel Kligler

(57)     ABSTRACT
A system (20) comprises a radiation source (48) and a controller (44). The controller is configured to designate multiple target regions (84) on an eye (25) of a patient (22) for irradiation with respective amounts of energy, to cause the radiation source to irradiate at least a first one of the target regions, to identify a change in the eye by processing an image of the eye subsequently to causing the radiation source to irradiate at least the first one of the target regions, and to refrain, in response to identifying the change, from causing the radiation source to irradiate a second one of the target regions, which has not yet been irradiated, with the
(Continued)

amount of energy designated for the second one of the target regions. Other embodiments are also described.

36 Claims, 9 Drawing Sheets

Related U.S. Application Data

(60) Provisional application No. 63/105,388, filed on Oct. 26, 2020.

(56) References Cited

U.S. PATENT DOCUMENTS

| | | | |
|---|---|---|---|
| 4,587,257 | A | 5/1986 | DeSantis et al. |
| 4,641,349 | A | 2/1987 | Flom et al. |
| 4,718,418 | A | 1/1988 | L'Esperance |
| 4,848,894 | A | 7/1989 | Buser et al. |
| 4,941,093 | A | 7/1990 | Marshall et al. |
| 4,966,452 | A | 10/1990 | Shields et al. |
| 5,049,147 | A | 9/1991 | Danon |
| 5,123,902 | A | 6/1992 | Muller et al. |
| 5,141,506 | A | 8/1992 | York |
| 5,151,909 | A | 9/1992 | Davenport et al. |
| 5,152,760 | A | 10/1992 | Latina |
| 5,370,641 | A | 12/1994 | O'Donnell, Jr. |
| 5,422,899 | A | 6/1995 | Freiberg et al. |
| 5,479,222 | A | 12/1995 | Volk et al. |
| 5,537,164 | A | 7/1996 | Smith |
| 5,549,596 | A | 8/1996 | Latina |
| 5,598,007 | A | 1/1997 | Bunce et al. |
| 5,786,883 | A | 7/1998 | Miller et al. |
| 5,865,830 | A | 2/1999 | Parel et al. |
| 5,982,789 | A | 11/1999 | Marshall et al. |
| 6,027,216 | A | 2/2000 | Guyton et al. |
| 6,030,376 | A | 2/2000 | Arashima et al. |
| 6,033,396 | A | 3/2000 | Huang et al. |
| 6,059,772 | A | 5/2000 | Hsia et al. |
| 6,090,100 | A | 7/2000 | Hohla |
| 6,090,102 | A * | 7/2000 | Telfair ................ A61F 9/00804 606/4 |
| 6,096,029 | A | 8/2000 | O'Donnell, Jr. |
| 6,099,521 | A | 8/2000 | Shadduck |
| 6,099,522 | A | 8/2000 | Knopp et al. |
| 6,146,375 | A | 11/2000 | Juhasz et al. |
| 6,159,202 | A | 12/2000 | Sumiya et al. |
| 6,210,399 | B1 | 4/2001 | Parel et al. |
| 6,258,082 | B1 | 7/2001 | Lin |
| 6,263,879 | B1 | 7/2001 | Lin |
| 6,267,752 | B1 | 7/2001 | Svetliza |
| 6,267,756 | B1 | 7/2001 | Feuerstein et al. |
| 6,286,960 | B1 | 9/2001 | Tomita |
| 6,319,274 | B1 | 11/2001 | Shadduck |
| 6,325,792 | B1 | 12/2001 | Swinger et al. |
| 6,414,980 | B1 | 7/2002 | Wang et al. |
| 6,454,763 | B1 | 9/2002 | Motter et al. |
| 6,514,241 | B1 | 2/2003 | Hsia et al. |
| 6,530,916 | B1 | 3/2003 | Shimmick |
| 6,569,104 | B2 | 5/2003 | Ono et al. |
| 6,585,723 | B1 | 7/2003 | Sumiya |
| 6,673,062 | B2 | 1/2004 | Yee et al. |
| 6,676,655 | B2 | 1/2004 | McDaniel |
| 6,685,317 | B2 | 2/2004 | Su et al. |
| 6,698,886 | B2 | 3/2004 | Pollack et al. |
| 6,736,806 | B2 | 5/2004 | Ruiz et al. |
| 6,761,713 | B2 | 7/2004 | Teichmann |
| 6,899,707 | B2 | 5/2005 | Scholler et al. |
| 6,942,656 | B2 | 9/2005 | Pawlowski et al. |
| 6,948,815 | B2 | 9/2005 | Neuberger |
| 6,979,328 | B2 | 12/2005 | Baerveldt et al. |
| 7,027,233 | B2 | 4/2006 | Goldstein et al. |
| 7,252,661 | B2 | 8/2007 | Nguyen et al. |
| 7,282,046 | B2 | 10/2007 | Simon |
| 7,353,829 | B1 | 4/2008 | Wachter et al. |
| 7,371,230 | B2 | 5/2008 | Webb et al. |

| | | | |
|---|---|---|---|
| 7,693,259 | B2 | 4/2010 | Gertner |
| 7,792,249 | B2 | 9/2010 | Gertner et al. |
| 8,004,764 | B2 | 8/2011 | Artsyukhovich et al. |
| 8,048,065 | B2 | 11/2011 | Grecu et al. |
| 8,109,635 | B2 | 2/2012 | Allon et al. |
| 8,160,113 | B2 | 4/2012 | Adams et al. |
| 8,403,921 | B2 | 3/2013 | Palankar et al. |
| 8,442,185 | B2 | 5/2013 | Gertner et al. |
| 8,465,478 | B2 | 6/2013 | Frey et al. |
| 8,475,433 | B2 | 7/2013 | Mrochen et al. |
| 8,545,020 | B2 | 10/2013 | Liesfeld et al. |
| 8,568,393 | B2 | 10/2013 | Palanker |
| 8,630,388 | B2 | 1/2014 | Gertner et al. |
| 8,679,100 | B2 | 3/2014 | Raksi et al. |
| 8,708,491 | B2 | 4/2014 | Frey et al. |
| 8,709,029 | B2 | 4/2014 | Griffis, III et al. |
| 8,771,261 | B2 | 7/2014 | Andersen et al. |
| 8,811,657 | B2 | 8/2014 | Teiwes et al. |
| 8,845,625 | B2 | 9/2014 | Angeley et al. |
| 8,903,468 | B2 | 12/2014 | Peyman |
| 8,920,407 | B2 | 12/2014 | Raksi et al. |
| 8,939,965 | B2 | 1/2015 | Liesfeld et al. |
| 8,968,279 | B2 | 3/2015 | Arnoldussen |
| 8,995,618 | B2 | 3/2015 | Gertner |
| 9,055,896 | B2 | 6/2015 | Amthor et al. |
| 9,192,780 | B2 | 11/2015 | McDaniel |
| 9,220,407 | B2 | 12/2015 | Yam et al. |
| 9,351,878 | B2 | 5/2016 | Muehlhoff et al. |
| 9,480,599 | B2 | 11/2016 | Degani et al. |
| 9,495,743 | B2 | 11/2016 | Angeley et al. |
| 9,504,609 | B2 | 11/2016 | Kurtz |
| 9,532,712 | B2 | 1/2017 | Liesfeld et al. |
| 9,622,911 | B2 | 4/2017 | Rubinfeld et al. |
| 9,782,232 | B1 | 10/2017 | Papac |
| 9,849,032 | B2 | 12/2017 | Schuele et al. |
| 9,849,034 | B2 | 12/2017 | Artsyukhovich et al. |
| 9,877,633 | B2 | 1/2018 | Zhao et al. |
| 9,889,043 | B2 | 2/2018 | Frey et al. |
| 9,968,483 | B2 | 5/2018 | Takeda et al. |
| 10,022,457 | B2 | 7/2018 | Peyman |
| 10,064,757 | B2 | 9/2018 | Berlin |
| 10,143,590 | B2 | 12/2018 | Dick et al. |
| 10,244,991 | B2 | 4/2019 | Shademan et al. |
| 10,258,507 | B2 | 4/2019 | Gonzalez et al. |
| 10,278,865 | B2 | 5/2019 | Luttrull et al. |
| 10,299,961 | B2 | 5/2019 | Luttrull et al. |
| 10,363,169 | B2 | 7/2019 | Belkin et al. |
| 10,441,465 | B2 | 10/2019 | Hart et al. |
| 10,449,091 | B2 | 10/2019 | Angeley et al. |
| 10,456,209 | B2 | 10/2019 | Peyman |
| 10,478,342 | B2 | 11/2019 | Dick et al. |
| 10,524,656 | B2 | 1/2020 | Wiltberger et al. |
| 10,617,564 | B1 | 4/2020 | Andersen et al. |
| 10,684,449 | B2 | 6/2020 | Curatu et al. |
| 10,702,416 | B2 | 7/2020 | Belkin et al. |
| 10,849,789 | B2 | 12/2020 | Dewey et al. |
| 10,925,768 | B2 | 2/2021 | Charles |
| 2001/0027314 | A1 | 10/2001 | Peyman |
| 2002/0013572 | A1 | 1/2002 | Berlin |
| 2002/0013573 | A1 | 1/2002 | Telfair et al. |
| 2002/0026179 | A1 | 2/2002 | Toh |
| 2003/0179344 | A1 | 9/2003 | Van de Velde |
| 2003/0225398 | A1 | 12/2003 | Zepkin et al. |
| 2004/0039378 | A1 | 2/2004 | Lin |
| 2004/0059321 | A1 | 3/2004 | Knopp et al. |
| 2004/0151217 | A1 * | 8/2004 | Yeik .................... B23K 26/034 372/69 |
| 2004/0196431 | A1 | 10/2004 | Farberov |
| 2005/0096639 | A1 | 5/2005 | Slatkine et al. |
| 2005/0107774 | A1 | 5/2005 | Lin |
| 2005/0185138 | A1 | 8/2005 | Wong et al. |
| 2005/0197655 | A1 | 9/2005 | Telfair et al. |
| 2005/0254009 | A1 | 11/2005 | Baker et al. |
| 2005/0286019 | A1 | 12/2005 | Wiltberger et al. |
| 2005/0288745 | A1 | 12/2005 | Andersen et al. |
| 2006/0100677 | A1 | 5/2006 | Blumenkranz et al. |
| 2006/0176913 | A1 | 8/2006 | Souhaite et al. |
| 2006/0195076 | A1 | 8/2006 | Blumenkranz et al. |
| 2006/0224147 | A1 | 10/2006 | Abe et al. |

(56)     References Cited

U.S. PATENT DOCUMENTS

| | | |
|---|---|---|
| 2006/0265030 A1 | 11/2006 | McDaniel |
| 2007/0081166 A1 | 4/2007 | Brown et al. |
| 2007/0129709 A1 | 6/2007 | Andersen et al. |
| 2007/0159600 A1 | 7/2007 | Gil et al. |
| 2007/0213693 A1 | 9/2007 | Plunkett |
| 2008/0027418 A1 | 1/2008 | Berry |
| 2008/0089481 A1 | 4/2008 | Gertner |
| 2008/0108934 A1 | 5/2008 | Berlin et al. |
| 2008/0161781 A1 | 7/2008 | McArdle et al. |
| 2008/0167642 A1 | 7/2008 | Palanker et al. |
| 2008/0204658 A1 | 8/2008 | Van Saarloos |
| 2008/0234667 A1 | 9/2008 | Lang et al. |
| 2008/0255546 A1 | 10/2008 | Orbachevski |
| 2009/0093798 A1* | 4/2009 | Charles .............. A61F 9/00823 606/4 |
| 2009/0137993 A1 | 5/2009 | Kurtz |
| 2009/0157062 A1 | 6/2009 | Hauger et al. |
| 2009/0247997 A1 | 10/2009 | Watanabe et al. |
| 2010/0002837 A1 | 1/2010 | Gertner et al. |
| 2010/0057059 A1 | 3/2010 | Makino |
| 2010/0076419 A1 | 3/2010 | Chew et al. |
| 2010/0142767 A1 | 6/2010 | Fleming |
| 2010/0324543 A1 | 12/2010 | Kurtz et al. |
| 2011/0144627 A1 | 6/2011 | Smith et al. |
| 2011/0172649 A1 | 7/2011 | Schuele et al. |
| 2011/0190741 A1 | 8/2011 | Deisinger et al. |
| 2012/0016349 A1 | 1/2012 | Brownell |
| 2012/0050308 A1 | 3/2012 | Nakano et al. |
| 2012/0083772 A1 | 4/2012 | Rubinfeld et al. |
| 2012/0089134 A1 | 4/2012 | Horvath et al. |
| 2012/0259321 A1 | 10/2012 | Vera et al. |
| 2012/0283557 A1 | 11/2012 | Berlin |
| 2013/0103011 A1 | 4/2013 | Grant et al. |
| 2013/0123761 A1 | 5/2013 | Belkin et al. |
| 2013/0158530 A1 | 6/2013 | Goldshleger et al. |
| 2013/0204236 A1 | 8/2013 | Awdeh |
| 2013/0218145 A1 | 8/2013 | Belkin et al. |
| 2013/0289450 A1 | 10/2013 | Homer |
| 2013/0317570 A1 | 11/2013 | Luttrull et al. |
| 2014/0094785 A1 | 4/2014 | Charles |
| 2014/0114297 A1 | 4/2014 | Woodley et al. |
| 2014/0128731 A1 | 5/2014 | Gonzalez et al. |
| 2014/0128851 A1 | 5/2014 | Wysopal |
| 2014/0128852 A1 | 5/2014 | Gooding et al. |
| 2014/0135747 A1 | 5/2014 | Donitzky et al. |
| 2014/0135753 A1 | 5/2014 | Feklistov et al. |
| 2014/0276681 A1 | 9/2014 | Schuele et al. |
| 2014/0307077 A1 | 10/2014 | Prabhakar |
| 2015/0164635 A1 | 6/2015 | Renke |
| 2015/0190276 A1 | 7/2015 | Ha et al. |
| 2015/0223683 A1 | 8/2015 | Davidovics et al. |
| 2015/0266706 A1 | 9/2015 | Hashimoto |
| 2015/0272782 A1 | 10/2015 | Schuele et al. |
| 2015/0313759 A1 | 11/2015 | Vera et al. |
| 2015/0366706 A1 | 12/2015 | Belkin et al. |
| 2016/0008169 A1 | 1/2016 | Yu |
| 2016/0008172 A1 | 1/2016 | Kahook |
| 2016/0067035 A1 | 3/2016 | Gontijo et al. |
| 2016/0067087 A1 | 3/2016 | Tedford et al. |
| 2016/0087402 A1* | 3/2016 | Tatah ................... H01S 5/0651 372/34 |
| 2016/0089232 A1 | 3/2016 | DeBoer et al. |
| 2016/0089269 A1 | 3/2016 | Horvath et al. |
| 2016/0095752 A1 | 4/2016 | Srinivasan et al. |
| 2016/0113816 A1 | 4/2016 | Herekar et al. |
| 2016/0346126 A1 | 12/2016 | Luttrull et al. |
| 2016/0354241 A1 | 12/2016 | Mordaunt et al. |
| 2016/0367399 A1 | 12/2016 | Goldshleger et al. |
| 2017/0000647 A1 | 1/2017 | Schuele et al. |
| 2017/0038284 A1 | 2/2017 | Nemati |
| 2017/0087014 A1 | 3/2017 | Potter, Jr. et al. |
| 2017/0127938 A1 | 5/2017 | Izatt et al. |
| 2017/0184875 A1 | 6/2017 | Newman |
| 2017/0246033 A1 | 8/2017 | Bor et al. |
| 2017/0252213 A1* | 9/2017 | Furuuchi ............. A61F 9/00821 |
| 2017/0340483 A1 | 11/2017 | Rill et al. |
| 2017/0360604 A1 | 12/2017 | Bach et al. |
| 2018/0085257 A1 | 3/2018 | Horvath et al. |
| 2018/0104477 A1 | 4/2018 | Kurtz et al. |
| 2018/0125708 A1 | 5/2018 | Bohme et al. |
| 2018/0168737 A1 | 6/2018 | Ren et al. |
| 2018/0207029 A1 | 7/2018 | Herekar et al. |
| 2018/0214305 A1 | 8/2018 | Schuele et al. |
| 2018/0221199 A1 | 8/2018 | Heacock |
| 2018/0235462 A1 | 8/2018 | Gooi et al. |
| 2018/0344527 A1 | 12/2018 | Palanker et al. |
| 2019/0078073 A1 | 3/2019 | Streeter et al. |
| 2019/0099291 A1 | 4/2019 | Herekar et al. |
| 2019/0105200 A1 | 4/2019 | Hipsley |
| 2019/0105519 A1 | 4/2019 | Herekar et al. |
| 2019/0117459 A1 | 4/2019 | Berlin |
| 2019/0142636 A1 | 5/2019 | Tedford et al. |
| 2019/0151146 A1 | 5/2019 | Kim |
| 2019/0247225 A1 | 8/2019 | Stobrawa et al. |
| 2019/0269554 A1 | 9/2019 | Goldshleger et al. |
| 2019/0343680 A1 | 11/2019 | Belkin et al. |
| 2019/0344076 A1 | 11/2019 | Irazoqui et al. |
| 2019/0358085 A1 | 11/2019 | Fu et al. |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0107724 A1 | 4/2020 | Wiltberger et al. |
| 2020/0146887 A1 | 5/2020 | Horvath et al. |
| 2020/0306080 A1 | 10/2020 | Herekar et al. |
| 2020/0345546 A1 | 11/2020 | Belkin et al. |
| 2020/0352785 A1 | 11/2020 | Holland et al. |
| 2020/0360187 A1 | 11/2020 | Schuele et al. |
| 2020/0379216 A1 | 12/2020 | Curatu et al. |
| 2021/0113373 A1 | 4/2021 | Sacks et al. |
| 2021/0267800 A1 | 9/2021 | Sacks et al. |
| 2021/0338484 A1 | 11/2021 | Hipsley |
| 2021/0393438 A1 | 12/2021 | Degani et al. |
| 2022/0031503 A1 | 2/2022 | Dorin et al. |
| 2022/0249861 A1 | 8/2022 | Belkin et al. |
| 2023/0201034 A1 | 6/2023 | Sacks et al. |
| 2023/0201037 A1 | 6/2023 | Barrett et al. |
| 2023/0226372 A1 | 7/2023 | Herekar et al. |

FOREIGN PATENT DOCUMENTS

| | | |
|---|---|---|
| AU | 2015315113 B2 | 3/2016 |
| CA | 2640203 A1 | 8/2007 |
| CN | 1579351 A | 2/2005 |
| CN | 101411607 A | 4/2009 |
| CN | 201537172 U | 8/2010 |
| CN | 102193182 A | 9/2011 |
| CN | 105138996 A | 12/2015 |
| CN | 205698218 U | 11/2016 |
| CN | 108024870 A | 1/2022 |
| DE | 202016006265 U1 | 3/2017 |
| EP | 0224322 A1 | 6/1987 |
| EP | 0651982 A1 | 5/1995 |
| EP | 0689811 A1 | 1/1996 |
| EP | 1602321 A1 | 12/2005 |
| EP | 2301421 A1 | 3/2011 |
| EP | 2301424 B1 | 3/2011 |
| EP | 2301425 B1 | 3/2011 |
| EP | 2602005 A1 | 6/2013 |
| EP | 1856774 B1 | 6/2016 |
| EP | 2695016 B1 | 3/2017 |
| EP | 2992931 B1 | 8/2017 |
| EP | 2391318 B1 | 12/2017 |
| EP | 3329839 A1 | 6/2018 |
| EP | 2729099 B1 | 11/2019 |
| EP | 3191040 B1 | 7/2020 |
| EP | 3517081 B1 | 11/2020 |
| EP | 2854729 B1 | 3/2021 |
| FR | 2655837 A1 | 6/1991 |
| JP | 2007151739 A | 6/2007 |
| JP | 2010506689 A | 3/2010 |
| JP | 2010148635 A | 7/2010 |
| JP | 2016013255 A | 1/2016 |
| JP | 2016507321 A | 3/2016 |
| JP | 2017506573 A | 3/2017 |

(56) References Cited

FOREIGN PATENT DOCUMENTS

| JP | 2017506944 A | 3/2017 |
|----|--------------|--------|
| JP | 2018051210 A | 4/2018 |
| KR | 20180106113 A | 10/2018 |
| KR | 20190022216 A | 3/2019 |
| RU | 2499582 C1 | 11/2013 |
| RU | 2553507 C1 | 6/2015 |
| WO | 9216259 A1 | 10/1992 |
| WO | 1993012727 A1 | 7/1993 |
| WO | 9316631 A1 | 9/1993 |
| WO | 9412092 A1 | 6/1994 |
| WO | 9416425 A1 | 7/1994 |
| WO | 9515134 A1 | 6/1995 |
| WO | 1998022016 A2 | 5/1998 |
| WO | 1998048746 A1 | 11/1998 |
| WO | 9918868 A1 | 4/1999 |
| WO | 0195842 A1 | 12/2001 |
| WO | 02064031 A2 | 8/2002 |
| WO | 02087442 A1 | 11/2002 |
| WO | 2014018104 A1 | 1/2004 |
| WO | 2004027487 A1 | 4/2004 |
| WO | 2006119349 A2 | 11/2006 |
| WO | 2006119584 A1 | 11/2006 |
| WO | 2006128038 A2 | 11/2006 |
| WO | 2007103349 A2 | 9/2007 |
| WO | 2008112236 A1 | 9/2008 |
| WO | 2008118198 A2 | 10/2008 |
| WO | 2010094353 A1 | 8/2010 |
| WO | 2010113193 A1 | 10/2010 |
| WO | 2011017002 A2 | 2/2011 |
| WO | 2011163508 A2 | 6/2011 |
| WO | 2011085274 A1 | 7/2011 |
| WO | 2011151812 A1 | 12/2011 |
| WO | 2013004255 A1 | 1/2013 |
| WO | 2013035091 A1 | 3/2013 |
| WO | 2013059481 A1 | 4/2013 |
| WO | 2013059564 A1 | 4/2013 |
| WO | 2013122711 A1 | 8/2013 |
| WO | 2013165689 A1 | 11/2013 |
| WO | 2014025862 A1 | 2/2014 |
| WO | 2014132162 A1 | 9/2014 |
| WO | 2014191031 A1 | 12/2014 |
| WO | 2015069197 A1 | 5/2015 |
| WO | 2015119888 A1 | 8/2015 |
| WO | 2015130821 A2 | 9/2015 |
| WO | 2015131135 A1 | 9/2015 |
| WO | 2016018864 A1 | 2/2016 |
| WO | 2016058931 A2 | 4/2016 |
| WO | 2016156760 A1 | 10/2016 |
| WO | 2016187436 A1 | 11/2016 |
| WO | 2016207739 A1 | 12/2016 |
| WO | 2017023296 A1 | 2/2017 |
| WO | 2017031570 A1 | 3/2017 |
| WO | 2017069819 A1 | 4/2017 |
| WO | 2018005796 A1 | 1/2018 |
| WO | 2018021780 A1 | 2/2018 |
| WO | 2018049246 A1 | 3/2018 |
| WO | 2018152020 A1 | 8/2018 |
| WO | 2018232397 A1 | 12/2018 |
| WO | 2019109125 A1 | 6/2019 |
| WO | 2020008323 A1 | 1/2020 |
| WO | 2020012841 A1 | 1/2020 |
| WO | 2020018242 A1 | 1/2020 |
| WO | 2020018436 A1 | 1/2020 |
| WO | 2020050308 A1 | 3/2020 |
| WO | 202093060 A2 | 5/2020 |
| WO | 2020089737 A1 | 5/2020 |
| WO | 2020093060 A2 | 5/2020 |
| WO | 2020183342 A1 | 9/2020 |
| WO | 2021026538 A1 | 2/2021 |
| WO | 2021048723 A1 | 3/2021 |
| WO | 2021155445 A1 | 8/2021 |
| WO | 2021170664 A1 | 9/2021 |
| WO | 2022223690 A1 | 10/2022 |

OTHER PUBLICATIONS

"Smart Selecta Duet—Your Smart Selection for Glaucoma Care," Product Brochure, pp. 1-6, The Lumenis Group of Companies, year 2018.

Rashad, "How to do YAG LASER Posterior Capsulotomy in Small Pupil?", YouTube Clip, p. 1, Jul. 19, 2020 https://www.youtube.com/watch?v=I2c39BoNBjM.

Quantel Medical, "Optimis II", datasheet, pp. 1-4, Aug. 5, 2022.

Variscite, "DART-MX8M", Datasheet, pp. 1-92, Feb. 2021.

Gazzard et al., "Selective Laser Trabeculoplasty versus Drops for Newly Diagnosed Ocular Hypertension and Glaucoma: The LiGHT RCT," Health Technology Assessment, NHS, vol. 23, issue 31, pp. 1-132, Jun. 2019.

Kelley et al., "Stem Cells in the Trabecular Meshwork: Present and Future Promises," Experimental Eye Research, vol. 88, issue 4, pp. 747-751, Apr. 2009.

Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.

Nowell et al., "Corneal Epithelial Stem Cells and their Niche at a Glance," Cell Science at a Glance, vol. 130, issue 6, pp. 1021-1025, year 2017.

Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.

Gonzalez et al., "Limbal Stem Cells: Identity, Developmental Origin, and Therapeutic Potential," WIREs Developmental Biology, Wiley, vol. 7, issue 2, pp. 1-23, Mar. 2018.

Sepehr, "Corneal Endothelial Cell Dysfunction: Etiologies and Management," Therapeutic Advances in Opthalmology, pp. 1-19, year 2018.

Espana et al., "Existence of Corneal Endothelial Slow-Cycling Cells," Investigative Ophthalmology & Visual Science, vol. 56, No. 6, pp. 3827-3837, Jun. 2015.

Walshe et al., "Serial Explant Culture Provides Novel Insights into the Potential Location and Phenotype of Corneal Endothelial Progenitor Cells," Experimental Eye Research, vol. 127, pp. 9-13, year 2014.

Pinnamaneni et al., "Concise Review: Stem Cells in the Corneal Stroma," Stem Cells, vol. 30, issue 6, pp. 1059-1063, year 2012.

International Application # PCT/IB2021/059821 Search Report dated Apr. 7, 2022.

Gophotonics, "NL200 series," Data Sheet, pp. 1-3, Jun. 29, 2017.

EP Application # 20201567.3 Office Action dated Jun. 6, 2023.

JP Application # 2020561860 Office Action dated Jun. 13, 2023.

JP Application # 2021516473 Office Action dated Jun. 20, 2023.

CN Application # 2020800563096 Office Action dated Jul. 1, 2023.

EP Application # 20864109.2 Search Report dated Aug. 10, 2023.

Root, "How to perform a Laser Iridotomy (Video)," pp. 1-14, year 2010, as downloaded from https://timroot.com/how-to-perform-a-laser-iridotomy-video/.

AU Application # 2022211843 Office Action dated Sep. 27, 2023.

AU Application # 2021311097 Office Action dated Sep. 28, 2023.

U.S. Appl. No. 17/427,926 Office Action dated Oct. 17, 2023.

JP Application # 2021536316 Office Action dated Oct. 24, 2023.

JP Application # 2020561860 Office Action dated Oct. 31, 2023.

JP Application # 2021516473 Office Action dated Nov. 7, 2023.

SG Application # 11202010437T Office Action Dec. 5, 2023.

U.S. Appl. No. 17/735,153 Office Action dated Dec. 18, 2023.

U.S. Appl. No. 17/136,052 Office Action dated Dec. 22, 2023.

U.S. Appl. No. 17/427,926 Office Action dated Dec. 22, 2023.

International Application # PCT/IB2023/060104 Search Report Dec. 26, 2023.

Sridhar, "Anatomy of Cornea and Ocular Surface," Indidan Journal of Ophthalmology, vol. 66, issue 2, pp. 190-194, year 2018.

JP Application # 2022567443 Office Action dated Dec. 17, 2024.

Kohnen et al., "Internal Anterior Chamber Diameter using Optical Coherence Tomography Compared with White-To-White Distances using Automated Measurements," Journal of Cataract & Refractive Surgery, vol. 32, pp. 1809-1813, Nov. 2006.

(56)                References Cited

OTHER PUBLICATIONS

Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.

Katta et al., "Optical Coherence Tomography Image-Guided Smart Laser Knife for Surgery," Lasers in Surgery and Medicine, Wiley Online Library, pp. 1-11, Jul. 2017.

Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.

Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.

Kim et at., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.

Hong et al., "Effect of Prophylactic Brimonidine Instillation on Bleeding during Strabismus Surgery in Adults," American Journal of Ophthalmology, vol. 144, No. 3, pp. 469-470, Sep. 2007.

Goldsmith et al., "Anterior Chamber Width Measurement by High-Speed Optical Coherence Tomography," Ophthalmology, vol. 112, No. 2, pp. 238-244, year 2005.

Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.

Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.

Radcliffe et al., "Energy Dose-Response in Selective Laser Trabeculoplasty: A Review," Journal of Glaucoma, vol. 31, pp. e49-e68, year 2022.

Gazzard, "A Brief Guide to Gonioscopy," Video Clip, Optometry today, pp. 1-2, May 21, 2015, as downloaded from https://www.youtube.com/watch?v=8yTTbHWxUik.

Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.

Nolan et al., "Gonioscopy skills and techniques," Community Eye Health Journal, vol. 34, No. 112, pp. 40-42, year 2021.

Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.

Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.

Prophotonix, "Green Laser Modules," Product Information, pp. 1-8, year 2024, as downloaded from https://www.prophotonix.com/led-and-laser-products/laser-modules/laser-modules-color/green-laser-modules/.

Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.

Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.

Bruce et al., "Zoom in on Gonioscopy," Review of Optometry, pp. 1-8, Sep. 1, 2016, as downloaded from https://www.reviewofoptometry.com/article/zoom-in-on-gonioscopy.

AU Application # 2022211843 Office Action dated Jan. 8, 2024.

JP Application # 2022508451 Office Action dated Mar. 5, 2024.

AU Application # 2021369792 Office Action dated Mar. 21, 2024.

Vogel et al., "Optical properties of human sclera, and their consequences for transscleral laser applications.", Lasers in Surgery and Medicine , vol. 11, pp. 331-340, year 1991.

Geffen et al., "Transscleral Selective Laser Trabeculoplasty Without a Gonioscopy Lens", Journal of Glaucoma, Inc, vol. 26, No. 3, pp. 201-207, Mar. 2017.

Das et al., "Sclera Recognition—A Survey", 2nd IAPR Asian Conference on Pattern Recognition, pp. 1-5, year 2013.

Kaya et al., "Designing A Pattern Stabilization Method Using Scleral Blood Vessels For Laser Eye Surgery", International Conference on Pattern Recognition, pp. 698-701, Istanbul, Turkey, Aug. 23-26, 2010.

Barkana et al., "Selective Laser Trabeculoplasty", Survey of Ophthalmology, vol. 52, No. 6, pp. 634-653, year 2007.

Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-but-difficult-to-get-right, pp. 22-24, year 2019.

Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.

Acott et al., "Trabecular Repopulation by Anterior Trabecular Meshwork Cells After Laser Trabeculoplasty", American Journal of Ophthalmology, vol. 107, issue 1, pp. 1-6, Jan. 1989.

Cao et al., "Peripheral Iridotomy," Medscape 25, pp. 1-12, Jun. 15, 2020.

Husain, "Laser Peripheral Iridotomy—Practical Points", YouTube presentation, p. 1, Sep. 28, 2016, downloaded from https://www.youtube.com/watch?=Azxzsv31yls.

Ivandic et al., "Early Diagnosis of Ocular Hypertension Using a Low-Intensity Laser Irradiation Test", Photomedicine and Laser Surgey, vol. 00, No. 00, pp. 1-5, year 2009.

Smith et al., "Light scatter from the central human cornea", Journal "Eye", issue 4, pp. 584-588, year 1990.

Turati et al., "Patterned Laser Trabeculoplasty", Ophthalmic Surgery, Lasers and Imaging , vol. 41, No. 5, pp. 538-545, year 2010.

Nozaki et al.,"Patterned Laser Trabeculoplasty with PASCAL streamline 577", Investigative Ophthalmology & Visual Science, vol. 54, p. 1867, Jun. 2013.

Acktar, "Magic Black Coatings", Product Information, pp. 1-6, year 2017.

Acktar, "Fractal Black Coating", Product Information, pp. 1-5, year 2017.

Cloudy Nights LLC, "Cloudy Nights—Equipment Discussions—ATM", Optics and DIY Forum, pp. 1-5, Feb. 15, 2015.

Defense Tech, "Anti-Laser Contact Lenses", Product Information, p. 1-1, Nov. 29, 2004.

IEC standard 60825-1, "Safety of Laser Products", Edition 1.2, pp. 1-122, years 2001-2008.

Laser Safety Industries, "Filter Specifications", pp. 1-5, year 2008.

Thorlabs, "Laser Safety Glasses", Product Information, p. 1, Nov. 3, 2014.

Surrey Nanosystems Ltd, "Vantablack", Data Sheet, pp. 1-4, Mar. 1, 2016.

EP Application # 21885460.2 Search Report dated Aug. 26, 2024.

EP Application # 19830473.5 Office Action dated Sep. 3, 2024.

U.S. Appl. No. 17/273,323 Office Action dated Oct. 30, 2024.

U.S. Appl. No. 17/427,926 Office Action dated Aug. 27, 2024.

Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.

Hong et al., "Repeat Selective Laser Trabeculoplasty," Journal of Glaucoma, vol. 18, issue 3, pp. 180-183, Mar. 2009.

Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.

(56)  References Cited

OTHER PUBLICATIONS

Franco et al., "Effect of Second SLT on IOP," Investigative Ophthalmology & Visual Science, vol. 48, pp. 1-2, May 2007.

Chen et al., "A Comparison between 90 degrees and 180 degrees Selective Laser Trabeculoplasty," Journal of Glaucoma, vol. 13, issue 1, p. 1, Feb. 2004.

Mequio et al., "Efficacy of Repeat Selective Laser Trabeculoplasty," Investigative Ophthalmology & Visual Science, vol. 48, p. 1, year 2007.

Grulkowski et al., "Anterior segment imaging with Spectral OCT system using a high-speed CMOS camera," Optics Express, vol. 17, No. 6, p. 4842-4858, year 2009.

Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.

Liu et al., "Real-time visual analysis of microvascular blood flow for critical care," CVPR2015 paper as Open Access Version, provided by the Computer Vision Foundation, pp. 2217-2225, year 2015.

Desco et al., "Effect of prophylactic brimonidine on bleeding complications after cataract surgery," European Journal of Ophthalmology, vol. 15, pp. 228-232, year 2005.

Pasquali et al., "Dilute brimonidine to improve patient comfort and subconjunctival hemorrhage after LASIK," Journal of Refractive Surgery, vol. 29, pp. 469-475, year 2013.

Sacks et al., "Non-contact direct selective laser trabeculoplasty: light propagation analysis," Biomedical Optics Express, vol. 11, pp. 2889-2904, year 2020.

Kasuga et al., "Trabecular Meshwork Length in Men and Women by Histological Assessment," Current Eye Research, Early Online, pp. 1-5, Jun. 2012.

Navilas Operator Manual, Document Version 2.10, 2012 OD-OS GmbH, pp. 1-94, Sep. 2012.

SensoMotoric Instruments GmbH (SMI), "SG 3000", Product Flyer, pp. 1-2, year 2010.

Ashik et al., "The precision of ophthalmic biometry using calipers," Canadian Journal of Ophthalmology, vol. 48, issue 6, pp. 1-13, Dec. 2013.

Balalzsi, "Noncontact Thermal Mode Nd:YAG Laser Transscleral Cyclocoagulation in the Treatment of Glaucoma," Ophthalmology, vol. 98, pp. 1858-1863, year 1991.

Leung et al., "Anterior chamber angle imaging with optical coherence tomography," Eye, vol. 25, pp. 261-267, year 2011.

Tasman et al., "The Wills Eye Hospital Atlas of Clinical Ophthalmology," Lippincott Williams & Wilkins, p. 158, year 2001.

Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.

Kara, "Bleeding in Retinal Images Using Image Processing", A Thesis submitted to the graduate school of applied sciences of Near East University, Nicosia, Larnaca, pp. 1-79, year 2019.

International Application # PCT/IB2023/061472 Search Report dated Feb. 29, 2024.

U.S. Appl. No. 17/427,926 Office Action dated May 9, 2024.

EP Application # 19877990.2 Office Oction dated May 13, 2024.

EP Application # 24158977.9 Search Report dated May 15, 2024.

EP Applicatian # 21845437.9 Search Report dated Jun. 19, 2024.

JP Application # 2023217477 Office Action dated Jul. 9, 2024.

U.S. Appl. No. 17/273,323 Office Action dated Jun. 18, 2024.

Chinese Office Action #202180071581.6 dated Apr. 25, 2025.

Australian Examination 1st Report, #2024205587 dated Jul. 10, 2025.

EP Communication pursuant to rules 70 (2) and 70a (2) EPC #25152129.0.

Extended European Search Report #25152129.0 dated Apr. 3, 2025.

JP Notice of Allowance # 2023-217477 dated May 7, 2025.

JP Office Action #2023-519588 dated Aug. 5, 2025.

JP Office Action #2022-567443 dated May 7, 2025.

Singapore Written Opinion #11202200506U dated Apr. 17, 2025.

* cited by examiner

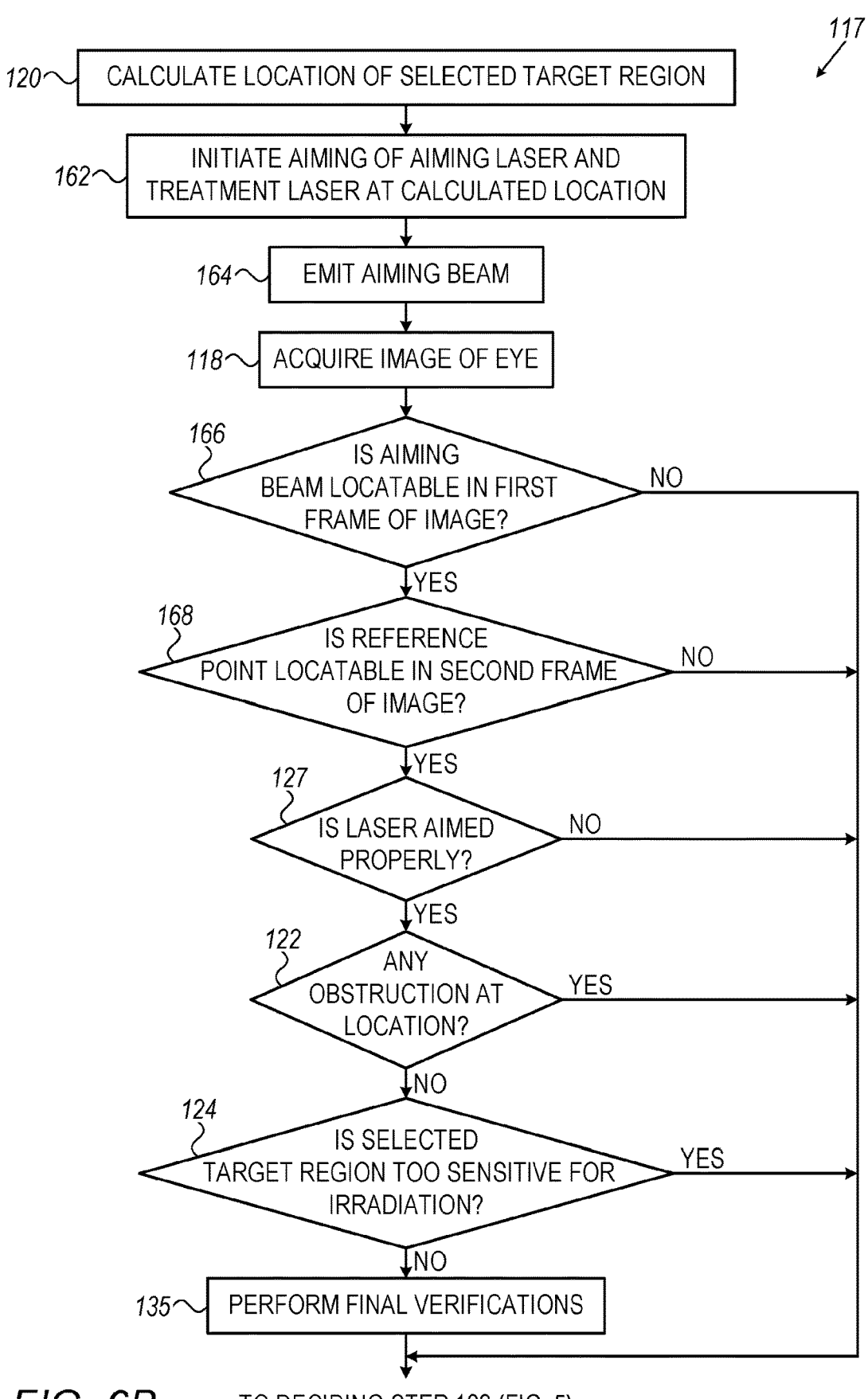

*117*

120 — CALCULATE LOCATION OF SELECTED TARGET REGION

162 — INITIATE AIMING OF AIMING LASER AND TREATMENT LASER AT CALCULATED LOCATION

164 — EMIT AIMING BEAM

118 — ACQUIRE IMAGE OF EYE

166 — IS AIMING BEAM LOCATABLE IN FIRST FRAME OF IMAGE? — NO

YES

168 — IS REFERENCE POINT LOCATABLE IN SECOND FRAME OF IMAGE? — NO

YES

127 — IS LASER AIMED PROPERLY? — NO

YES

122 — ANY OBSTRUCTION AT LOCATION? — YES

NO

124 — IS SELECTED TARGET REGION TOO SENSITIVE FOR IRRADIATION? — YES

NO

135 — PERFORM FINAL VERIFICATIONS

*FIG. 6B*      TO DECIDING STEP 128 (FIG. 5)

AVOIDING BLOOD VESSELS DURING DIRECT SELECTIVE LASER TRABECULOPLASTY

CROSS-REFERENCE TO RELATED APPLICATIONS

The present application is a continuation in part of U.S. application Ser. No. 17/136,052, entitled "Avoiding blood vessels during direct selective laser trabeculoplasty," filed Dec. 29, 2020, whose disclosure is incorporated herein by reference, and additionally claims the benefit of U.S. Provisional Application 63/105,388, entitled "Vasoconstrictors for use in laser eye surgery," filed Oct. 26, 2020, whose disclosure is incorporated herein by reference.

FIELD OF THE INVENTION

The present invention relates to ophthalmological devices and methods for the treatment of glaucoma, ocular hypertension (OHT), and other diseases.

BACKGROUND

U.S. Pat. No. 5,422,899 describes an optically pumped mid-infrared solid-state laser with high pulse repetition rate for use in laser surgery. The laser produces a wavelength between 1.7 and 4.0 microns, and is optically pumped.

U.S. Pat. No. 6,761,713 describes a medical laser unit including at least one laser body being made of laser material. A first type of a pump light source is designed and arranged to continuously excite the laser material and to generate continuous laser radiation. A second type of a pump light source is designed and arranged to excite the laser material by pulses and to generate pulsed laser radiation. A transmitting unit is designed and arranged to transmit the continuous laser radiation and the pulsed laser radiation to a surgical application site. More particularly, the medical laser unit has two modes of operation, a first mode for cutting with continuous laser radiation and a second mode for fragmenting with pulsed laser radiation of short time and high power laser pulses.

U.S. Pat. No. 8,160,113 describes output pulses from an optical system having a seed source and an optical amplifier coupled to the seed source, which may be controlled by controlling a power of a seed signal from the seed source. The seed signal may be varied between a minimum value and a maximum value in a way that the seed signal exhibits one or more pulse bursts. Each pulse burst may contain one or more pulses. During an inter-pulse period between successive pulses within a pulse burst or between successive pulse bursts, the power of the seed signal may be adjusted to an intermediate value that is greater than the minimum value and less than the maximum value. The intermediate value is chosen to control a gain in the optical amplifier such that a pulse or pulse burst that follows the period exhibits a desired behavior.

U.S. Pat. No. 5,982,789 describes a diode pumped doubling system employing a pump diode, a crystal and doubler in a laser cavity with the diode, and operated in a pulsed or low duty cycle pumping regimen, while the cavity length is sufficiently short to stabilize the transient responses to pulsed diode operation and produce stable and known or controlled energy output under the non-CW pumping regimen. In a preferred embodiment, the device employs a doubler which is clamped across its non-critical axis, and is operated with a control system which creates isotherms in the active mode volume. The controller operates one or more separate heat sources and/or sinks to preheat the diode source or doubling crystal to maintain an oriented thermal gradient, and the rate or direction at which the isotherm migrates across the mode volume is controlled in accordance with the forthcoming pulse sequence to maintain effectively stable conditions during laser operation. The thermal control system may include sink, heater and control elements for pre-heating the laser diode before actuation, and during quiet intervals.

U.S. Pat. No. 5,151,909 describes a laser system using non-linear crystals for second harmonic generation and solid state gain media, which is operated under data processor control so that a plurality of pump power modes are available. The data processor modulates the pump power in a low power mode, and supplies continuous pump power in combination with Q-switching in a high power mode. Alternatively, modulation may be used in both low power and high power modes, with the parameters of the modulation adjusted under program control. Second harmonic generation without a Q-switch in high power modes can be achieved as well.

U.S. Pat. No. 6,414,980 describes a method for operating an extracavity frequency-converted solid-state laser for performing a laser processing operation. The laser has a laser-resonator including an optically-pumped gain-medium. The resonator is configured to compensate for a predetermined range of thermal lensing in the gain-medium. An optically-nonlinear crystal located outside the resonator converts fundamental laser radiation delivered by the resonator into frequency converted radiation. The laser processing operation is performed by a train of pulses of the frequency-converted radiation having sufficient power to perform the processing operation. The power of frequency-converted radiation is dependent on delivery parameters of the laser radiation from the laser-resonator. The laser is operated in a manner which provides that the resonator delivers effectively the same average power of fundamental laser radiation before and during the laser processing operation. This provides that thermal-lensing in the gain-medium is within the predetermined range before and during a laser processing operation. Delivery parameters of the laser radiation before and during the processing operation are varied such that power of frequency-converted radiation generated before the processing operating is insufficient to perform a laser processing operation.

In a laser trabeculoplasty procedure, a laser irradiates the trabecular meshwork in an eye of a patient with one or more treatment beams, thus lowering the intraocular pressure in the eye.

SUMMARY OF THE INVENTION

There is provided, in accordance with some embodiments of the present invention, a system including a radiation source and a controller. The controller is configured to designate multiple target regions on an eye of a patient for irradiation with respective amounts of energy. The controller is further configured to cause the radiation source to irradiate at least a first one of the target regions. The controller is further configured to identify a change in the eye, subsequently to causing the radiation source to irradiate at least the first one of the target regions, by processing an image of the eye. The controller is further configured to refrain from causing the radiation source to irradiate a second one of the target regions, which has not yet been irradiated, with the amount of energy designated for the second one of the target regions, in response to identifying the change.

In some embodiments, the controller is configured to refrain from causing the radiation source to irradiate the second one of the target regions by:

designating a new target region, and causing the radiation source to irradiate the new target region instead of the second one of the target regions.

In some embodiments, the controller is configured to refrain from causing the radiation source to irradiate the second one of the target regions with the amount of energy designated for the second one of the target regions by causing the radiation source to irradiate the second one of the target regions with another amount of energy that is less than the designated amount.

In some embodiments, the change includes bleeding.

In some embodiments, the change includes swelling.

In some embodiments, the change includes a change in color.

In some embodiments, the change includes a formation of one or more bubbles.

In some embodiments, the controller is configured to refrain from causing the radiation source to irradiate the second one of the target regions in response to a distance between the second one of the target regions and another region of the eye.

In some embodiments, the controller is further configured to identify an anatomical feature at the second one of the target regions, and the controller is configured to refrain from causing the radiation source to irradiate the second one of the target regions in response to identifying the anatomical feature.

In some embodiments, the controller is further configured to calculate a predicted measure of overlap between a radiation beam irradiating the second one of the target regions and the anatomical feature, and the controller is configured to refrain from causing the radiation source to irradiate the second one of the target regions in response to the predicted measure of overlap.

In some embodiments, the anatomical feature is a second-target-region anatomical feature, the controller is further configured to identify a first-target-region anatomical feature at the first one of the target regions, and the controller is configured to refrain from causing the radiation source to irradiate the second one of the target regions in response to identifying the first-target-region anatomical feature.

In some embodiments, the controller is configured to refrain from causing the radiation source to irradiate the second one of the target regions in response to the first-target-region anatomical feature and the second-target-region anatomical feature being of the same type.

In some embodiments, the controller is further configured to:

calculate an estimated measure of overlap between (a) a first radiation beam that irradiated the first one of the target regions and (b) the first-target-region anatomical feature, and calculate a predicted measure of overlap between (a) a second radiation beam irradiating the second one of the target regions and (b) the first-target-region anatomical feature, and the controller is configured to refrain from causing the radiation source to irradiate the second one of the target regions in response to the predicted measure of overlap and the estimated measure of overlap.

In some embodiments, the controller is further configured to:

calculate an estimated amount of energy delivered by a first radiation beam to the first-target-region anatomical feature, and calculate a predicted amount of energy delivered by a second radiation beam to the second-target-region anatomical feature, and the controller is configured to refrain from causing the radiation source to irradiate the second one of the target regions in response to the predicted amount of energy and the estimated amount of energy.

In some embodiments, the controller is further configured to calculate a risk measure associated with irradiating the second one of the target regions, and the controller is configured to refrain from causing the radiation source to irradiate the second one of the target regions in response to the risk measure.

In some embodiments, the controller is configured to calculate the risk measure based on a medical profile of the patient.

In some embodiments, the controller is further configured to identify an anatomical feature at the second one of the target regions, and the controller is configured to calculate the risk measure based on a type of the second anatomical feature.

There is further provided, in accordance with some embodiments of the present invention, a method including designating multiple target regions on an eye of a patient for irradiation with respective amounts of energy. The method further includes causing a radiation source to irradiate at least a first one of the target regions. The method further includes, subsequently to causing the radiation source to irradiate at least the first one of the target regions, by processing an image of the eye, identifying a change in the eye. The method further includes, in response to identifying the change, refraining from causing the radiation source to irradiate a second one of the target regions, which has not yet been irradiated, with the amount of energy designated for the second one of the target regions.

There is further provided, in accordance with some embodiments of the present invention, a system, including a radiation source and a controller. The controller is configured to acquire an image of an eye, to identify, in the image, multiple edge points at different respective angles relative to a reference point located on the eye radially inward from the edge points, each of the edge points lying on an edge of a respective blood vessel, to define multiple target regions on the eye between the reference point and the edge points, and to cause the radiation source to irradiate the target regions.

In some embodiments, the reference point is located at a center of an iris of the eye.

In some embodiments, the reference point is located at a center of a limbus of the eye.

In some embodiments, the reference point is located at a center of a pupil of the eye.

In some embodiments, for each angle, the edge of the respective blood vessel is closer to the reference point than is any other edge of any blood vessel at the angle.

In some embodiments, the controller is configured to define the target regions by:

defining at least one treatment path between the edge points and the reference point, and defining the target regions such that each of the target regions lies on the treatment path.

In some embodiments, the controller is configured to define the treatment path such that a shortest distance between any one of the edge points and the treatment path is at least 0.001 mm.

In some embodiments, the controller is configured to define the treatment path by:

defining at least one curve passing through the edge points, offsetting the curve toward the reference point, and defining the treatment path responsively to the offset curve.

In some embodiments, the controller is configured to define the treatment path responsively to the offset curve by defining the treatment path as a perimeter of a predetermined shape inscribed within the offset curve.

In some embodiments, the predetermined shape is an ellipse.

In some embodiments, the controller is configured to define the treatment path responsively to the offset curve by defining the treatment path as a perimeter of a predetermined shape of maximal area inscribed within the offset curve.

In some embodiments, the controller is configured to define the treatment path responsively to the offset curve by defining the treatment path as a perimeter of a predetermined shape of maximal area centered at the reference point and inscribed within the offset curve.

In some embodiments, the controller is configured to define the treatment path responsively to the offset curve by defining the treatment path as a closed curve inscribed within the offset curve and having a shape of a limbus of the eye.

There is further provided, in accordance with some embodiments of the present invention, a method including acquiring an image of an eye, identifying, in the image, multiple edge points at different respective angles relative to a reference point located on the eye radially inward from the edge points, each of the edge points lying on an edge of a respective blood vessel, defining multiple target regions on the eye between the reference point and the edge points, and causing a radiation source to irradiate the target regions.

There is further provided, in accordance with some embodiments of the present invention, a system including a radiation source and a controller. The controller is configured to acquire an image of an eye, to identify, in the image, multiple edge points at different respective angles relative to a reference point located on the eye radially inward from the edge points, each of the edge points lying on an edge of a respective blood vessel, to define at least one curve passing through the edge points, and to offset the curve toward the reference point. The controller is further configured to receive from a user, while displaying the offset curve to the user, a definition of multiple target regions on the eye, and to cause the radiation source to irradiate the target regions.

There is further provided, in accordance with some embodiments of the present invention, a method including acquiring an image of an eye, identifying, in the image, multiple edge points at different respective angles relative to a reference point located on the eye radially inward from the edge points, each of the edge points lying on an edge of a respective blood vessel, defining at least one curve passing through the edge points, and offsetting the curve toward the reference point. The method further includes, while displaying the offset curve to a user, receiving, from the user, a definition of multiple target regions on the eye, and causing a radiation source to irradiate the target regions.

There is further provided, in accordance with some embodiments of the present invention, a method including administering an α2 agonist to an eye of a patient and, less than 40 minutes following the administering of the α2 agonist, treating an eye of the patient with laser radiation.

In some embodiments, treating the eye of the patient includes treating the eye of the patient by irradiating a trabecular meshwork of the eye with the laser radiation.

In some embodiments, treating the eye of the patient includes treating the eye of the patient less than 30 minutes following the administering of the α2 agonist.

In some embodiments, treating the eye of the patient includes treating the eye of the patient in response to an indication, from a controller, that blood vessels of the eye were sufficiently constricted by the α2 agonist.

There is further provided, in accordance with some embodiments of the present invention, an α2 agonist for use in a method of vasoconstricting an eye of a patient, the α2 agonist being administered to the patient less than 40 minutes prior to treating the eye with laser radiation.

There is further provided, in accordance with some embodiments of the present invention, a system, including a camera, configured to acquire an image of an eye of a patient prior to a treatment of the eye with laser radiation, and a controller. The controller is configured to compute, by processing the image, a constriction measure indicating an extent to which blood vessels of the eye were constricted by an α2 agonist. The controller is further configured to output, in response to the constriction measure passing a predefined threshold, an indication that the blood vessels were sufficiently constricted by the α2 agonist.

There is further provided, in accordance with some embodiments of the present invention, a system, including a laser, including a pump source and a lasing medium, and a controller. The controller is configured to designate multiple target regions on an eye of a patient for irradiation, in sequence, by the laser. The controller is further configured to start the irradiation of the target regions, by driving the pump source to begin pumping the lasing medium with a train of lasing-causing pulses, each of which is configured to cause the lasing medium to lase. The controller is further configured to cause the pump source, subsequently to starting the irradiation of the target regions, to substitute one or more heating pulses for one of the lasing-causing pulses, the heating pulses being configured to heat the lasing medium without causing the lasing medium to lase.

In some embodiments, the controller is further configured to cause the pump source, prior to starting the irradiation of the target regions, to heat the lasing medium without causing the lasing medium to lase.

In some embodiments, a total energy of the heating pulses is between 70% and 100% of a lasing-causing-pulse energy of each of the lasing-causing pulses.

In some embodiments, the one or more heating pulses consist of N>1 heating pulses.

In some embodiments, each of the heating pulses has a heating-pulse duration of DO/N, DO being a lasing-causing-pulse duration of each of the lasing-causing pulses.

In some embodiments, each of the heating pulses has a peak power equal to that of each of the lasing-causing pulses.

In some embodiments, the train is periodic with a period T, and the controller is configured to cause the pump source to substitute the heating pulses at times {k*T/N}, k=0 . . .

N−1 from a time at which the one of the lasing-causing pulses was to have been pumped.

In some embodiments, the controller is configured to cause the pump source to substitute the heating pulses in response to a signal indicating an error.

In some embodiments, the controller is further configured to process one or more images of the eye acquired by a camera, and the controller is configured to cause the pump source to substitute the heating pulses in response to processing the images.

In some embodiments, the controller is configured to identify an obstruction of the eye by processing the images, and the controller is configured to cause the pump source to substitute the heating pulses in response to identifying the obstruction.

In some embodiments, the controller is configured to identify a change in the eye by processing the images, and the controller is configured to cause the pump source to substitute the heating pulses in response to identifying the change.

In some embodiments, the change includes a formation of one or more bubbles.

In some embodiments, the controller is configured to identify a reference-point location of a reference point on the eye by processing the images, the controller is further configured to:

based on the reference-point location, calculate a target-region location of one of the target regions, and ascertain that the laser is not aimed at the target-region location, and the controller is configured to cause the pump source to substitute the heating pulses in response to the ascertaining.

In some embodiments, the system further includes one or more motors, the controller is further configured to aim the laser using the motors, and the controller is configured to ascertain that the laser is not aimed at the target-region location in response to respective signals from respective encoders of the motors.

In some embodiments, the laser is a treatment laser, the system further includes an aiming laser, the controller is further configured to:

cause the aiming laser to emit an aiming beam at a location at which the treatment laser is aimed, and identify an aiming-beam location of the aiming beam by processing the images, and the controller is configured to ascertain that the treatment laser is not aimed at the target-region location based on a displacement between the aiming-beam location and the target-region location.

In some embodiments, a wavelength of the aiming beam is greater than 700 nm.

In some embodiments, the images include a first image, which is acquired while the aiming beam is emitted such that the aiming beam appears in the first image, and a second image, which is acquired before or after the aiming beam is emitted such that the aiming beam does not appear in the second image, the controller is configured to identify the aiming-beam location in the first image, and the controller is configured to identify the reference-point location in the second image.

In some embodiments, the images consist of a single image including a first frame, in which the aiming beam appears, and a second frame, in which the aiming beam does not appear, the controller is configured to identify the aiming-beam location in the first frame, and the controller is configured to identify the reference-point location in the second frame.

There is further provided, in accordance with some embodiments of the present invention, a method including designating multiple target regions on an eye of a patient for irradiation, in sequence, by a laser. The method further includes starting the irradiation of the target regions, by driving a pump source to begin pumping a lasing medium of the laser with a train of lasing-causing pulses, each of which is configured to cause the lasing medium to lase. The method further includes, subsequently to starting the irradiation of the target regions, causing the pump source to substitute one or more heating pulses for one of the lasing-causing pulses, the heating pulses being configured to heat the lasing medium without causing the lasing medium to lase.

The present invention will be more fully understood from the following detailed description of embodiments thereof, taken together with the drawings, in which:

BRIEF DESCRIPTION OF THE DRAWINGS

FIGS. 6A-B are flow diagrams for an image-processing step, in accordance with different respective embodiments of the present invention;

DETAILED DESCRIPTION OF EMBODIMENTS

Overview

Figure 1:
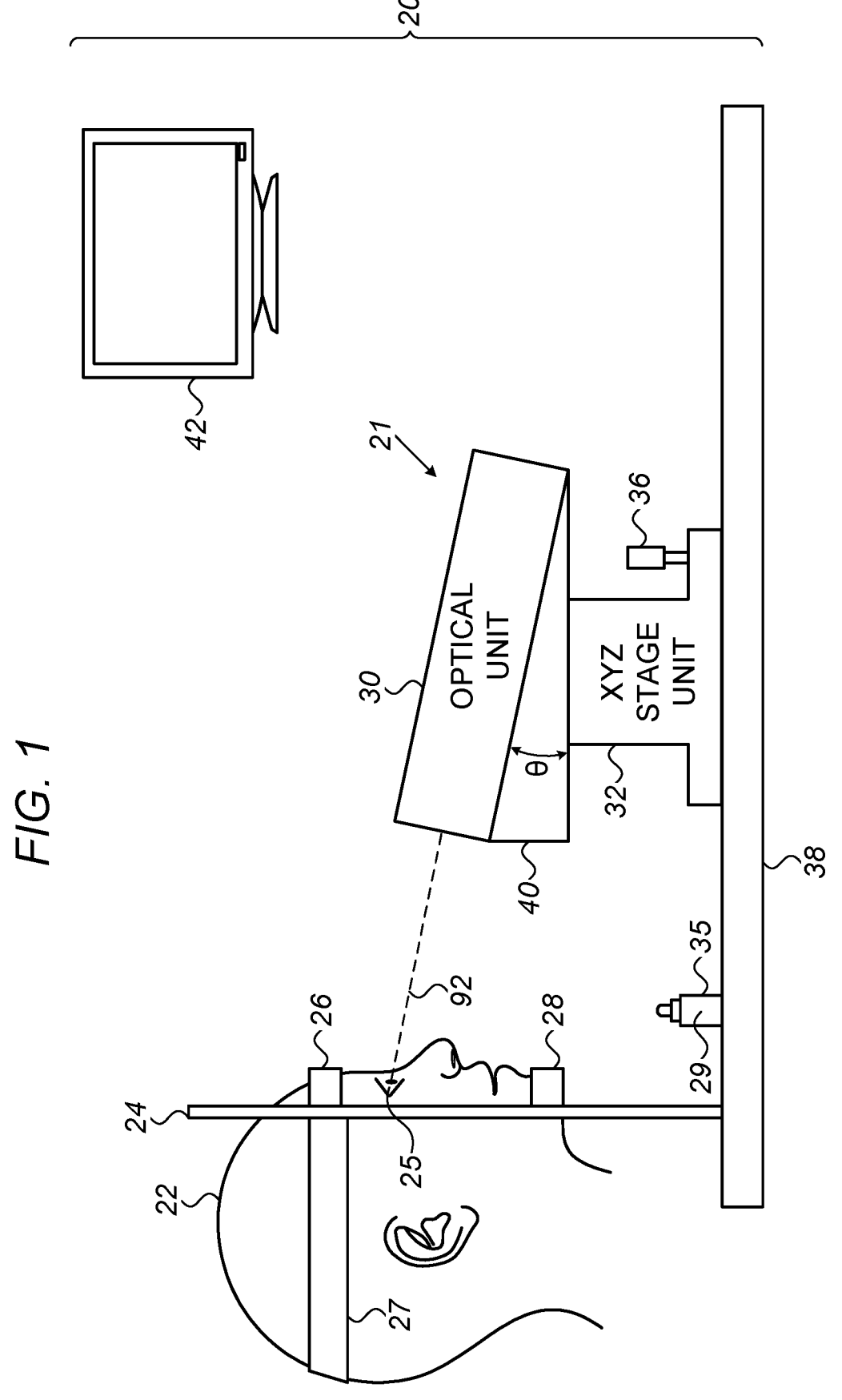
FIG. 1 is a schematic illustration of a system for performing a trabeculoplasty procedure, in accordance with some embodiments of the present invention.

When performing a laser trabeculoplasty on an eye, it is desirable to avoid irradiating blood vessels and other sensitive anatomy, due to the risk of bleeding and/or other adverse effects.

To address this challenge, embodiments of the present invention provide a technique for defining a treatment path that avoids the blood vessels of the eye. Subsequently to defining the treatment path, multiple target regions on the treatment path are defined, and the target regions are then irradiated.

To define the treatment path, a controller first identifies multiple points on the inner edges of blood vessels surrounding the limbus of the eye. Subsequently, the controller defines a curve passing through the points. The controller then offsets the curve inward, toward the center the eye. Finally, the controller inscribes the treatment path within the offset curve.

Notwithstanding the above, in some cases it may not be possible to define the treatment path as described above, e.g., due to an unusual distribution of blood vessels in the eye. Moreover, irradiation of sensitive areas other than blood vessels, such as growths, may also cause adverse effects.

Hypothetically, in view of this challenge, it might be possible to cut out portions of the treatment path that pass through blood vessels and other sensitive areas. However, as the present inventors have observed, it is generally impossible to know, a priori, the degree of sensitivity of an eye to radiation; for example, in some patients, even a direct hit of a laser beam on a blood vessel does not cause bleeding. Thus, avoiding all sensitive areas of the eye may, for some patients, unnecessarily reduce the efficacy of the treatment.

To address this challenge, embodiments of the present invention allow the treatment path to pass through sensitive areas, but continually monitor the eye, using suitable image-processing techniques, as the treatment proceeds. If any problematic change (e.g., bleeding) in the eye is observed, the controller evaluates, for each upcoming target region, the likelihood that irradiation of the upcoming target region will cause a similar change. In response to a high likelihood, the controller may shift or skip the upcoming target region. Thus, advantageously, the treatment path is modified selectively, without unnecessarily compromising the efficacy of the treatment.

For example, in response to observing a change at an irradiated target region, the controller may calculate a risk measure that depends on the type of sensitive anatomical feature at the irradiated target region (if such a feature exists), an estimated amount of radiation energy delivered to this sensitive anatomical feature, the type of sensitive anatomical feature at the upcoming target region (if such a feature exists), and an estimated amount of radiation energy that will be delivered to this sensitive anatomical feature. In response to the risk measure exceeding a predefined threshold, the controller may shift or skip the upcoming target region.

Alternatively or additionally, to reduce the amount of bleeding that occurs (e.g., to avoid causing any bleeding), the eye may be treated with a vasoconstricting α2 agonist, such as apraclonidine and/or brimonidine, before (e.g., less than 40 minutes before) the eye is irradiated. Following the administration of the α2 agonist, the controller, by processing images of the eye, may monitor the extent to which the blood vessels of the eye were constricted. In response to ascertaining that the blood vessels were sufficiently constricted, the controller may output an indication that the irradiation of the eye may begin.

In addition to monitoring the eye for problematic changes, the controller, using suitable image-processing techniques, continually checks for any obstacles lying along the treatment path. In response to detecting an obstacle, one or more target regions may be shifted or skipped.

Typically, immediately before the irradiation of each target region, the controller checks whether the laser is aimed at the location of the target region, accounting for any motion of the eye subsequent to the definition of the target region. (This check is typically performed in addition to checking for any changes to, or obstructions of, the eye as described above.) In the event that the laser is not aimed at the location or that the location could not be calculated, the controller aborts the impending irradiation. The irradiation of the target region may then be attempted again, after another image of the eye is acquired and processed. Alternatively, the target region may be skipped.

To check whether the laser is properly aimed, the controller may process signals received from the encoders of the motors that orient the beam-directing elements used to aim the laser. Alternatively or additionally, the controller may process an image of the eye acquired by a camera so as to locate an aiming beam, which impinges on the eye at the location at which the laser is aimed. In such embodiments, the aiming beam may be invisible to the patient (though visible to the camera), such that the aiming beam does not disturb the patient. Alternatively or additionally, the aiming beam may be configured and/or controlled so as not to interfere with the motion-tracking of the eye. For example, the camera may comprise a filter matrix that filters the wavelength of the aiming beam, such that the image includes a first frame in which the aiming beam appears and a second frame in which the aiming beam does not appear. Alternatively, the controller may acquire a first image while the aiming beam is emitted, and a second image while the aiming beam is not emitted. The controller may then locate the aiming beam in the first image or frame, but track motion of the eye based on the second image or frame.

In some embodiments, in response to deciding to abort the impending irradiation of a target region (e.g., due to an obstruction, a change such as bleeding, or improper aiming of the laser), the controller drives the pump source of the laser to pump the lasing medium of the laser with one or more heating pulses. Typically, the total energy of the heating pulses is approximately equal to the energy that would have been delivered to the lasing medium had the controller decided to proceed with the impending irradiation. However, this total energy is spread over a sufficiently large amount of time such that the lasing medium does not lase. Thus, advantageously, thermal equilibrium of the laser may be maintained until the target region (or, if the target region is to be skipped, the next target region) is irradiated. Alternatively or additionally, prior to beginning the treatment, the lasing medium may be pumped with heating pulses, such that thermal equilibrium is reached prior to the firing of the first treatment beam. On the other hand, if the lasing medium were left unheated for a period of time, the irradiation energy of at least the first treatment beam fired by the laser following the period of time might be less than desired, and/or the beam profile or beam aiming might become unstable.

System Description

Figure 2:
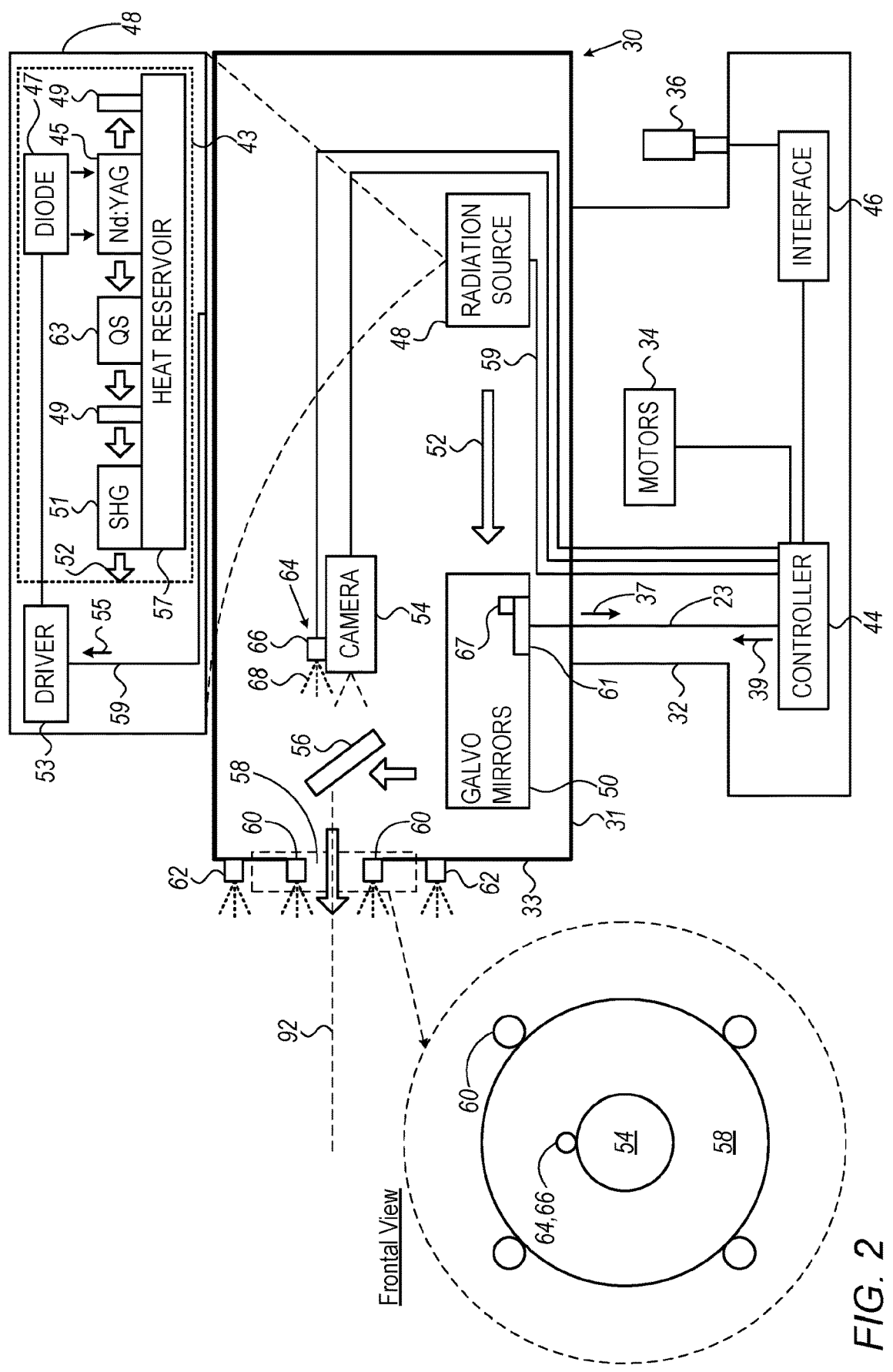
FIG. 2 is a schematic illustration of a trabeculoplasty device, in accordance with some embodiments of the present invention.

Reference is initially made to FIG. 1, which is a schematic illustration of a system 20, comprising a trabeculoplasty device 21, for performing a trabeculoplasty procedure, in accordance with some embodiments of the present invention. Reference is further made to FIG. 2, which is a schematic illustration of trabeculoplasty device 21, in accordance with some embodiments of the present invention.

Trabeculoplasty device 21 comprises an optical unit 30 and a controller 44. Optical unit 30 comprises a radiation source 48, which is configured to irradiate an eye 25 of a patient 22 (e.g., the trabecular meshwork of eye 25) with one or more treatment beams 52.

Typically, radiation source 48 comprises a treatment laser 43, such as an Ekspla™ NL204-0.5K-SH laser. Treatment laser 43 comprises a lasing medium 45, which may comprise, for example, a semiconductor, glass, or a crystal, such as a neodymium-doped yttrium aluminum garnet (Nd:YAG) crystal. Lasing medium 45 may be pumped by any suitable pump source 47, such as a laser diode. The pumping may be optical, electrical, or of any other suitable type. Laser 43 further comprises a plurality of mirrors 49 arranged to define a stable or unstable resonating cavity. (Each mirror 49 may be a standalone element, or it may comprise a reflective coating that coats another element.) Laser 43 further comprises a heat reservoir 57, which removes heat from lasing medium 45.

In some embodiments, the laser further comprises a Q-switch (QS) 63. Alternatively or additionally, the laser may comprise a second-harmonic generation (SHG) crystal 51, which converts the wavelength emitted by lasing medium 45 to another wavelength suitable for treatment. (SHG crystal 51 may be internal or external to the resonating cavity.) The laser may be modified to include an attenuator, an energy meter, and/or a mechanical shutter, which is typically external to the resonating cavity.

Typically, the radiation source further comprises a driver 53, and controller 44 drives pump source 47, via driver 53, to pump lasing medium 45. In particular, driver 53 receives control signals 55, typically over a cable 59, from controller 44. In response to control signals 55, the driver outputs electrical driving signals to pump source 47, and the pump source pumps the lasing medium in response thereto. In other embodiments, the controller drives pump source 47 directly, by outputting driving signals to the pump source.

Optical unit 30 further comprises one or more beam-directing elements, comprising, for example, one or more (e.g., two) galvo mirrors 50, which may be referred to collectively as a "galvo scanner." Before the emission of each treatment beam 52, controller 44 aims treatment laser 43 at the desired target region on eye 25 by orienting the beam-directing elements so as to direct the beam toward the target region. (Since each treatment beam impinges on the eye with a non-infinitesimal spot size, the present application generally describes each beam as impinging on a "region" of the eye, rather than impinging at a "point" on the eye.) Thus, for example, the beam may be deflected by galvo mirrors 50 toward a beam combiner 56, and then deflected by the beam combiner such that the beam impinges on the target region. The beam thus follows a path 92, which extends from the most downstream of the optical components in optical unit 30—such as beam combiner 56—to eye 25.

Typically, the controller orients the beam-directing elements (thus aiming the laser) by communicating (e.g., over a cable 23) control signals 39 to respective aiming motors 61 of the beam-directing elements. Typically, the controller receives (e.g., over cable 23 or a different cable) feedback signals 37, which indicate the respective orientations of the beam-directing elements, from respective encoders 67 of aiming motors 61.

In some embodiments, the treatment beams comprise visible light. Alternatively or additionally, the treatment beams may comprise non-visible electromagnetic radiation, such as microwave radiation, infrared radiation, X-ray radiation, gamma radiation, or ultraviolet radiation. Typically, the wavelength of the treatment beams is between 200 and 11000 nm, e.g., 500-850 nm, such as 520-540 nm, e.g., 532 nm. The spatial profile of each treatment beam 52 on the eye may be elliptical (e.g., circular), square, or of any other suitable shape.

In some embodiments, radiation source 48 further comprises an aiming laser, configured to emit visible or invisible (e.g., infrared) aiming beams. The aiming laser sufficiently overlaps treatment laser 43 such that, for any orientation of the beam-directing elements, the beam-directing elements direct the aiming beams and treatment beams to the same location. Thus, the aiming laser may facilitate the aiming of the treatment laser, as further described below with reference to FIG. 6B.

Alternatively or additionally to a laser, the radiation source may comprise any other suitable emitter configured to emit treatment beams or aiming beams.

Optical unit 30 further comprises a camera 54, which is used by controller 44 to acquire images of the eye. As shown in FIG. 2, camera 54 is typically aligned, at least approximately, with path 92; for example, the angle between path 92 and a hypothetical line extending from eye 25 to the camera may be less than 15 degrees. In some embodiments, the camera is positioned behind beam combiner 56, such that the camera receives light via the beam combiner. In other embodiments, the camera is offset from the beam combiner.

Before the procedure, camera 54 acquires at least one image of eye 25. Based on the image, controller 44 may define the target regions of the eye that are to be irradiated, as further described below with reference to FIGS. 3-4. Alternatively or additionally, based on the image, controller 44 may identify one or more blood vessels or other anatomical features of the eye, as further described below with reference to FIGS. 4-5.

Subsequently, during the procedure, camera 54 may acquire multiple images of the patient's eye at a relatively high frequency. Controller 44 may process these images and, in response thereto, control radiation source 48 and the beam-directing elements so as to irradiate the target regions of the eye while avoiding obstructions and potentially-sensitive anatomical features, as further described below with reference to FIGS. 6A-B and FIG. 7.

In general, camera 54 may comprise one or more imaging sensors of any suitable type(s), such as a charge-coupled device (CCD) sensor, a complementary metal-oxide-semiconductor (CMOS) sensor, an optical coherence tomography (OCT) sensor, and/or a hyperspectral image sensor. Using the sensors, the camera may acquire two-dimensional or three-dimensional images of any suitable type, such as monochrome images, color images (based, for example, on three color frames), multispectral images, hyperspectral images, optical coherence tomography (OCT) images, or images produced by fusing multiple images of different respective types.

In some embodiments, optical unit 30 further comprises a light source 66, which is aligned, at least approximately, with path 92. For example, the angle between path 92 and a hypothetical line extending from the end of path 92 on eye 25 to light source 66 may be less than 20 degrees, such as less than 10 degrees. Light source 66 is configured to function as a fixation target 64 by transmitting visible fixation light 68, thus helping to stabilize the position of the eye.

In particular, prior to the procedure, patient 22 is instructed to fixate eye 25 on light source 66. Subsequently, during the procedure, by virtue of light source 66 transmitting fixation light 68, eye 25 fixates on the light source, such that the eye's line-of-sight is approximately coincident with path 92 (due to the light source being approximately aligned with the path) and the eye is relatively stable. While the eye fixates on the light source, the radiation source irradiates the eye with treatment beams 52.

In some embodiments, light source 66 comprises a light emitter, such as a light emitting diode (LED). In other embodiments, the light source comprises a reflector config-ured to reflect light emitted from a light emitter.

Typically, the wavelength of fixation light 68, which may be higher or lower than that of the treatment beams, is between 350 and 850 nm. For example, fixation light 68 may be orange or red, with a wavelength of 600-750 nm, while the treatment beams may be green, with a wavelength of 527-537 nm.

Typically, the optical unit comprises an optical bench, and at least some of the aforementioned optical components belonging to the optical unit, such as the radiation source, the galvo mirrors, and the beam combiner, are coupled to the optical bench. Typically, the optical unit further comprises a front face 33, through which the treatment beams and the fixation light pass. For example, optical unit 30 may com-prise an encasement 31, which at least partially encases the optical bench and comprises front face 33. (Encasement 31 may be made of a plastic, a metal, and/or any other suitable material.) Alternatively, front face 33 may be attached to, or may be an integral part of, the optical bench.

In some embodiments, front face 33 is shaped to define an opening 58, through which the treatment beams and the fixation light pass. In other embodiments, the front face comprises an exit window in lieu of opening 58, such that fixation light 68 and treatment beams 52 pass through the exit window. The exit window may be made of a plastic, a glass, or any other suitable material.

Typically, optical unit 30 further comprises one or more illumination sources 60 comprising, for example, one or more LEDs, such as white-light or infrared LEDs. For example, the optical unit may comprise a ring of LEDs surrounding opening 58. In such embodiments, controller 44 may cause illumination sources 60 to intermittently flash light at the eye, as described in US Patent Application Publication 2021/0267800, whose disclosure is incorporated herein by reference. This flashing may facilitate the imaging performed by the camera, and, by virtue of the brightness of the flashing, may further help constrict the pupil of the eye without causing damage to the eye or discomfort to the patient. (For ease of illustration, the electrical connection between controller 44 and illumination sources 60 is not shown explicitly in FIG. 2.) In some embodiments, illumi-nation sources 60 are coupled to front face 33, as shown in FIG. 2.

To facilitate positioning the optical unit, the optical unit may comprise a plurality of beam emitters 62 (comprising, for example, respective laser diodes), which are configured to shine a plurality of triangulating range-finding beams on the eye, e.g., as described in US Patent Application Publi-cation 2021/0267800, whose disclosure is incorporated herein by reference. In some embodiments, beam emitters 62 are coupled to front face 33, as shown in FIG. 2. In other embodiments, beam emitters 62 are coupled directly to the optical bench.

Optical unit 30 is mounted onto an XYZ stage unit 32, which is controlled by a control mechanism 36, such as a joystick. Using control mechanism 36, the user of system 20, such as an ophthalmic surgeon, may position the optical unit (e.g., by adjusting the distance of the optical unit from the eye) prior to treating the eye. In some embodiments, XYZ stage unit 32 comprises locking elements configured to inhibit motion of the stage unit following the positioning of the stage unit.

In some embodiments, XYZ stage unit 32 comprises one or more motors 34, and control mechanism 36 is connected to interface circuitry 46. As the user manipulates the control mechanism, interface circuitry 46 translates this activity into appropriate electronic signals, and outputs these signals to controller 44. In response to the signals, the controller controls the motors of the XYZ stage unit.

In other embodiments, XYZ stage unit 32 is controlled manually by manipulating the control mechanism. In such embodiments, the XYZ stage unit may comprise a set of gears instead of motors 34.

System 20 further comprises a headrest 24, comprising a forehead rest 26 and a chinrest 28. During the trabeculo-plasty procedure, patient 22 presses his forehead against forehead rest 26 while resting his chin on chinrest 28. In some embodiments, headrest 24 further comprises an immo-bilization strap 27, configured to secure the patient's head from behind and thus keep the patient's head pressed against the headrest.

In some embodiments, as shown in FIG. 1, headrest 24 and XYZ stage unit 32 are both mounted onto a surface 38, such as a tray or tabletop. (In some such embodiments, the headrest is L-shaped, and is attached to the side, rather than the top, of surface 38.) In other embodiments, the XYZ stage unit is mounted onto surface 38, and the headrest is attached to the XYZ stage unit.

Typically, as shown in FIG. 1, while irradiating the patient's eye, the optical unit is directed obliquely upward toward the eye while the eye gazes obliquely downward toward the optical unit, such that path 92 is oblique. For example, the path may be oriented at an angle θ of between five and twenty degrees with respect to the horizontal. Advantageously, this orientation reduces occlusion of the patient's eye by the patient's upper eyelid and associated anatomy when the patient's head rests against the headrest.

In some embodiments, as shown in FIG. 1, the oblique orientation of path 92 is achieved by virtue of the optical unit being mounted on a wedge 40, which is mounted on the XYZ stage unit. In other words, the optical unit is mounted onto the XYZ stage unit via wedge 40. (Wedge 40 is omitted from FIG. 2.)

Alternatively or additionally to angling the optical unit, the patient's head may be tilted backward so as to reduce occlusion of the patient's eye.

System 20 further comprises a monitor 42, configured to display the images of the eye acquired by the camera. Monitor 42 may be attached to optical unit 30 or disposed at any other suitable location, such as on surface 38 next to device 21. In some embodiments, monitor 42 comprises a touch screen, and the user inputs commands to the system via the touch screen. Alternatively or additionally, system 20 may comprise any other suitable input devices, such as a keyboard or a mouse, which may be used by the user.

In some embodiments, monitor 42 is connected directly to controller 44 over a wired or wireless communication inter-face. In other embodiments, monitor 42 is connected to controller 44 via an external processor, such as a processor belonging to a standard desktop computer.

In some embodiments, as shown in FIG. 2, controller 44 is disposed within XYZ stage unit 32. In other embodiments, controller 44 is disposed externally to the XYZ stage unit. Alternatively or additionally, the controller may coopera-tively perform at least some of the functionality described herein with another, external processor.

In some embodiments, prior to the irradiation of eye 25, an α2 agonist 29 (FIG. 1) is administered to the eye. α2 agonist 29 may comprise, for example, apraclonidine and/or brimonidine. Typically, the α2 agonist is administered to the eye by dropping eye drops 35, which comprise the α2 agonist, into the eye.

Following the administering of α2 agonist 29, the α2 agonist constricts the blood vessels of the eye. Subsequently to the blood vessels being sufficiently constricted, the eye is irradiated with treatment beams 52. Typically, the blood vessels are sufficiently constricted, and hence the irradiation is performed, less than 40 minutes (e.g., less than 30, 20, 10, or 5 minutes), following the administering of the α2 agonist.

In some embodiments, an α2 agonist is administered at least twice. First (e.g., at around 45-60 minutes before the anticipated start time of the radiation treatment), an α2 agonist is administered to the eye so as to mitigate any possible spikes in intraocular pressure. Next, the same α2 agonist, or a different α2 agonist, is administered, typically less than 40 minutes (e.g., less than 30, 20, 10, or 5 minutes) before the anticipated start time. If sufficient constriction is not achieved after a predetermined amount of time, the same α2 agonist, or a different α2 agonist, is administered. Following a predetermined amount of time (which is typically less than 40 minutes, such as less than 30, 20, 10, or 5 minutes), the treatment is performed.

In some embodiments, the user of system 20 assesses whether the blood vessels of the eye are sufficiently constricted, without any help from controller 44.

In other embodiments, controller 44 assists the user based on an image acquired by camera 54. In particular, the controller, by processing the image, computes a constriction measure indicating the extent to which the blood vessels were constricted. (In some embodiments, only the green and/or blue frame of the image are processed for this purpose.) In response to the constriction measure passing a predefined threshold, the controller outputs an indication that the blood vessels were sufficiently constricted by the α2 agonist. For example, the controller may display a message on monitor 42 indicating that the radiation treatment may proceed. (The message need not explicitly mention the constriction.) In response to the indication, the user may begin the treatment. Alternatively, if the constriction measure does not pass the threshold, the controller outputs an indication that the same α2 agonist, or a different α2 agonist, should be administered.

In some embodiments, the constriction measure is based on the percentage of pixels within a predefined distance from the limbus 86 (FIG. 3) of the eye whose gray levels are greater than a predefined threshold (e.g., 230). Alternatively or additionally, the constriction measure may be based on the number and/or density of detected blood vessels, the average or maximum width of the detected blood vessels, and/or any other suitable statistic. To detect blood vessels in the image, the controller may use any of the techniques described below with reference to FIG. 4.

In some embodiments, at least some of the functionality of controller 44, as described herein, is implemented in hardware, e.g., using one or more fixed-function or general-purpose integrated circuits, Application-Specific Integrated Circuits (ASICs), and/or Field-Programmable Gate Arrays (FPGAs). Alternatively or additionally, controller 44 may perform at least some of the functionality described herein by executing software and/or firmware code. For example, controller 44 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein.

In some embodiments, the controller comprises a system on module (SOM), such as the Varisite™ DART-MX8M.

Defining the Target Regions

Figure 3:
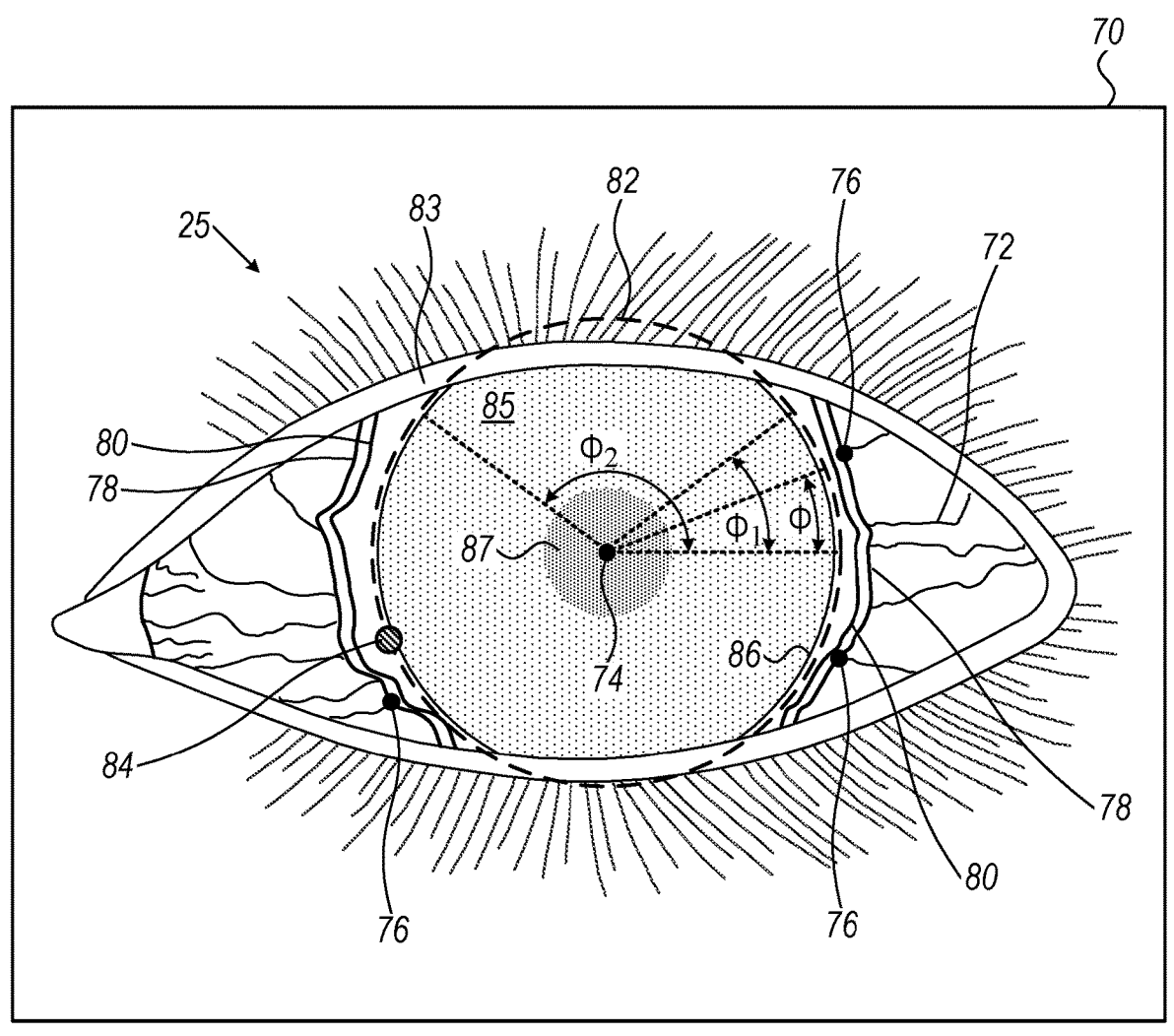
FIG. 3 is a schematic illustration of a technique for defining target regions on an eye, in accordance with some embodiments of the present invention.

Reference is now made to FIG. 3, which is a schematic illustration of a technique for defining target regions 84 on eye 25, in accordance with some embodiments of the present invention.

Typically, camera 54 (FIG. 2) acquires at least one image 70 of eye 25 prior to the treatment of the eye. In some embodiments, based on image 70, controller 44 defines target regions 84 such that the target regions do not lie over any blood vessels 72 visible in the image. (The target regions might, nonetheless, lie over blood vessels that are too small or deep to be visible in the image.)

To define the target regions, the controller first identifies, in image 70, multiple edge points 76, each of which lies on an edge of a respective blood vessel 72. Edge points 76 lie at different respective angles φ relative to a reference point 74 located on the eye radially inward from the edge points. Typically, for each angle, the edge on which the edge point lies is closer to reference point 74 than is any other edge of any blood vessel at the angle. (Typically, at least 50 edge points 76 are identified; for simplicity, however, FIG. 3 shows only three edge points 76.)

Subsequently to identifying the edge points, the controller defines target regions 84 between the reference point and the edge points. (Typically, at least 50 target regions are identified; for simplicity, however, FIG. 3 shows only one target region.) For example, the controller may first define at least one treatment path 82 between the edge points and the reference point, and then define the target regions such that each of the target regions lies on treatment path 82 (e.g., such that the center of each of the target regions lies on the treatment path). Successive target regions may be spaced apart from one another by any suitable angle, such as 2-4 degrees. For example, for a 360-degree treatment path, the controller may define between 90 and 180 target regions. (It is noted that, depending on the size of each target region and the spacing angle, successive target regions may overlap with one another.)

In some embodiments, the controller defines a respective edge point and target region for each angle belonging to a predefined set of angles. For those angles at which no blood-vessel edge can be identified, the controller defines a synthetic edge point, which does not actually lie at any blood-vessel edge, at a predefined distance from the reference point.

Typically, the treatment path is defined such that the shortest distance between any one of the edge points and the treatment path is at least 0.1 mm, such as between 0.1 and 1 mm, so as to provide sufficient distance between the target regions and the blood vessels.

In some embodiments, to define the treatment path, the controller first defines at least one curve 78 passing through edge points 76, e.g., using any suitable spline interpolation method known in the art. Subsequently, the controller offsets curve 78 toward the reference point, e.g., by a distance of between 0.001 and 1 mm, so as to define an offset curve 80. Subsequently, the controller defines the treatment path responsively to offset curve 80.

For example, at least a portion of the treatment path may be identical to at least a portion of the offset curve. Alternatively, the treatment path may be defined as the perimeter of a predetermined shape, such as an ellipse (e.g., a circle), inscribed within the offset curve and having any suitable center. For example, the treatment path may be defined as the perimeter of a predetermined shape of maximal area, or a predetermined shape of maximal area centered at reference point 74, inscribed within the offset curve. As yet another alternative, the treatment path may be defined as a closed curve inscribed within the offset curve and having the shape of the limbus 86 of the eye. As yet another alternative, the treatment path may be defined by smoothing offset curve 80 and/or offsetting the offset curve toward the reference point.

In some cases, as shown in FIG. 3, the patient's eyelids obscure the blood vessels within one or more ranges of angles. In such cases, the controller typically defines multiple curves 78 (and hence, multiple offset curves 80), each passing through a different respective exposed range of angles. Subsequently, based on the offset curves, the controller may define a closed treatment path, as described above. Nonetheless, the controller may refrain from defining any target regions within the obscured ranges of angles (along with, optionally, small angular ranges adjacent to the obscured ranges, so as to provide a margin of safety). For example, in the scenario shown in FIG. 3, the controller may refrain from defining any target regions between 01 and $\#_2$, given that the patient's upper eyelid 83 obscures blood vessels within this range of angles.

In other cases, the density of edge points within a particular range of angles may be less than a predefined threshold density required by whichever curve-fitting algorithm is used to define curve 78, despite this range of angles being exposed. (The low density may result from inability to identify a sufficient number of blood vessels, e.g., due to the patient being in a vasoconstricted state.) In such cases, the controller may define supplementary points lying on limbus 86 within the range of angles, so as to achieve the threshold density. Subsequently, the controller may define curve 78 such that the curve passes through the edge points and the supplementary points.

Typically, subsequently to defining the target regions, the controller overlays, on image 70, respective markers indicating the target regions. (Optionally, a marker indicating the treatment path may also be overlaid on the image.) The controller may then allow the user to adjust any of the target regions as required, and then indicate to the controller that the target regions are approved.

Alternatively or additionally, the controller may perform a simulated irradiation of the target regions. For example, the controller may communicate control signals 39 to aiming motors 61 (FIG. 2) so as to aim the treatment laser at each of the target regions in sequence. The controller may then process signals from encoders 67 (FIG. 2) so as to verify that the laser is actually aimed at each of the target regions. Alternatively or additionally, the controller may overlay, over a live sequence of images of the eye, respective markers indicating the locations at which the laser is aimed, such that the user may verify the aiming (including verifying that any motion of the eye is accounted for). Alternatively or additionally, for embodiments in which the radiation source comprises an aiming laser, the controller may cause the aiming laser to emit an aiming beam at each of the target regions in sequence, as described in US Patent Application Publication 2021/0267800, whose disclosure is incorporated herein by reference. The controller may then verify, by image processing, that the aiming beam impinges on each of the target regions. Alternatively or additionally, the controller may display a live sequence of images of the eye in which the aiming beam is visible, such that the user may verify the aiming.

Following approval of the target regions by the user and/or verification of the aiming by the controller and/or user, the controller causes the treatment laser to irradiate the target regions.

Figure 4:
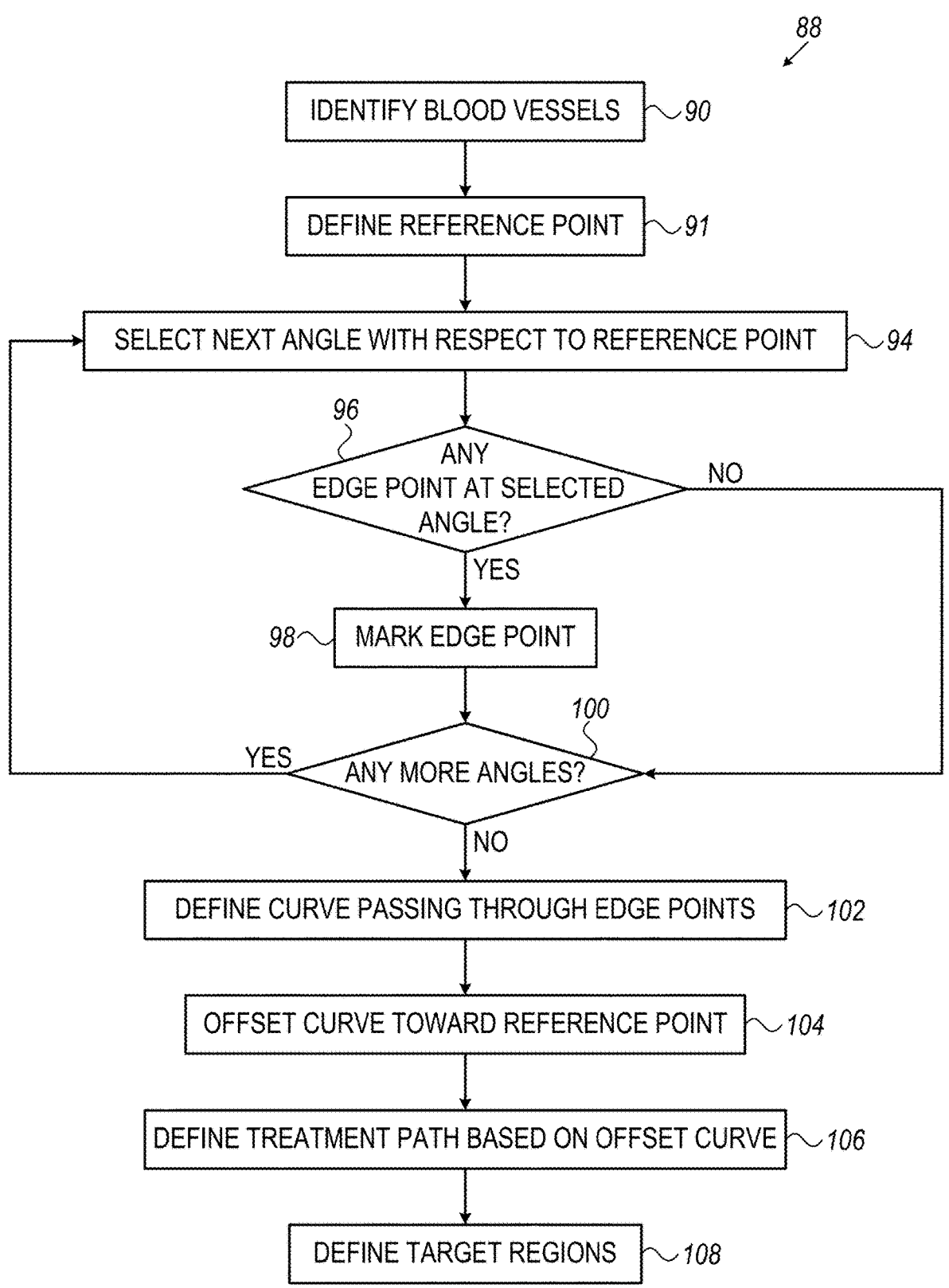
FIG. 4 is a flow diagram for an algorithm for defining target regions, in accordance with some embodiments of the present invention.

For further details regarding the definition of target regions 84, reference is now additionally made to FIG. 4, which is a flow diagram for an algorithm 88 for defining target regions 84, in accordance with some embodiments of the present invention.

Per algorithm 88, the controller first identifies blood vessels in image 70, at a blood-vessel-identifying step 90. To identify the blood vessels, the controller may use segmentation, edge detection, feature enhancement, pattern recognition, and/or any other suitable image-processing techniques. Such techniques are described, for example, in Das, Abhijit, et al., "Sclera recognition-a survey," 2013 2nd IAPR Asian Conference on Pattern Recognition, IEEE, 2013, whose disclosure is incorporated herein by reference.

Subsequently, at a reference-point-defining step 91, the controller defines reference point 74. For example, the controller may identify the iris 85 or pupil 87 of the eye (e.g., using color segmentation), and then place reference point 74 at the center of iris 85 or pupil 87. Alternatively, the controller may identify limbus 86 (e.g., using edge detection or maximum gradient detection), and then place the reference point at the center of the limbus. Alternatively, while image 70 is displayed on display 41 (FIG. 1), a user of system 20, using any suitable user interface (e.g., a mouse), may indicate the desired location of the reference point. In response thereto, the controller may place the reference point at the desired location. The controller may further calculate and store the offset of this location from the center of the iris, the center of the pupil, the center of the limbus, or any other anatomical point identifiable by image processing.

Subsequently, the controller iterates through a plurality of angles with respect to the reference point. Each angle is selected at an angle-selecting step 94. Subsequently to selecting the angle, the controller checks, at a checking step 96, whether there is any edge point at the selected angle. (This check is based on the controller having identified the blood vessels at blood-vessel-identifying step 90.) If yes, the controller marks the edge point, at an edge-point-marking step 98. Subsequently, or if there is no edge point at the selected angle, the controller checks, at another checking step 100, whether any more non-yet-selected angles remain. If yes, the controller returns to angle-selecting step 94.

In general, the controller may select any suitable angles. For example, the controller may define 0° with respect to any arbitrary axis (such as a horizontal axis, as shown in FIG. 3). Subsequently, during each $i^{th}$ iteration for i=1 . . . M, the controller may select $(i-1)*\Delta\theta$, where $\Delta\theta$ may be 0.5, F, or any other suitable value. M, the number of iterations, may be chosen such that 360° lies between $(M-1)*\Delta\theta$ and $M*\Delta\theta$.

Subsequently to marking the edge points, the controller, at a curve-defining step 102, defines curve 78. The controller then offsets curve 78 toward the reference point, at a curve-offsetting step 104. Subsequently, at a treatment-path-defining step 106, the controller defines the treatment path based on offset curve 80. Finally, the controller defines the target regions, at a target-region-defining step 108. Typically, each target region is specified as an offset from reference point 74 or any other suitable reference point. (The offset may be specified in terms of a radial or Cartesian coordinate system.)

In alternate embodiments, the controller displays offset curve 80 to the user (by superimposing the offset curve over image 70, over another still image of the eye, or over a live stream of such images), but does not define any target regions. Rather, while the controller displays the offset curve, the controller receives, from the user, the definition of the target regions. For example, the user may define the target regions by clicking a mouse button at each desired target-region location. In response thereto, the controller designates the target regions for irradiation, in sequence, by treatment laser 43 (FIG. 2).

Performing the Treatment

Figure 5:
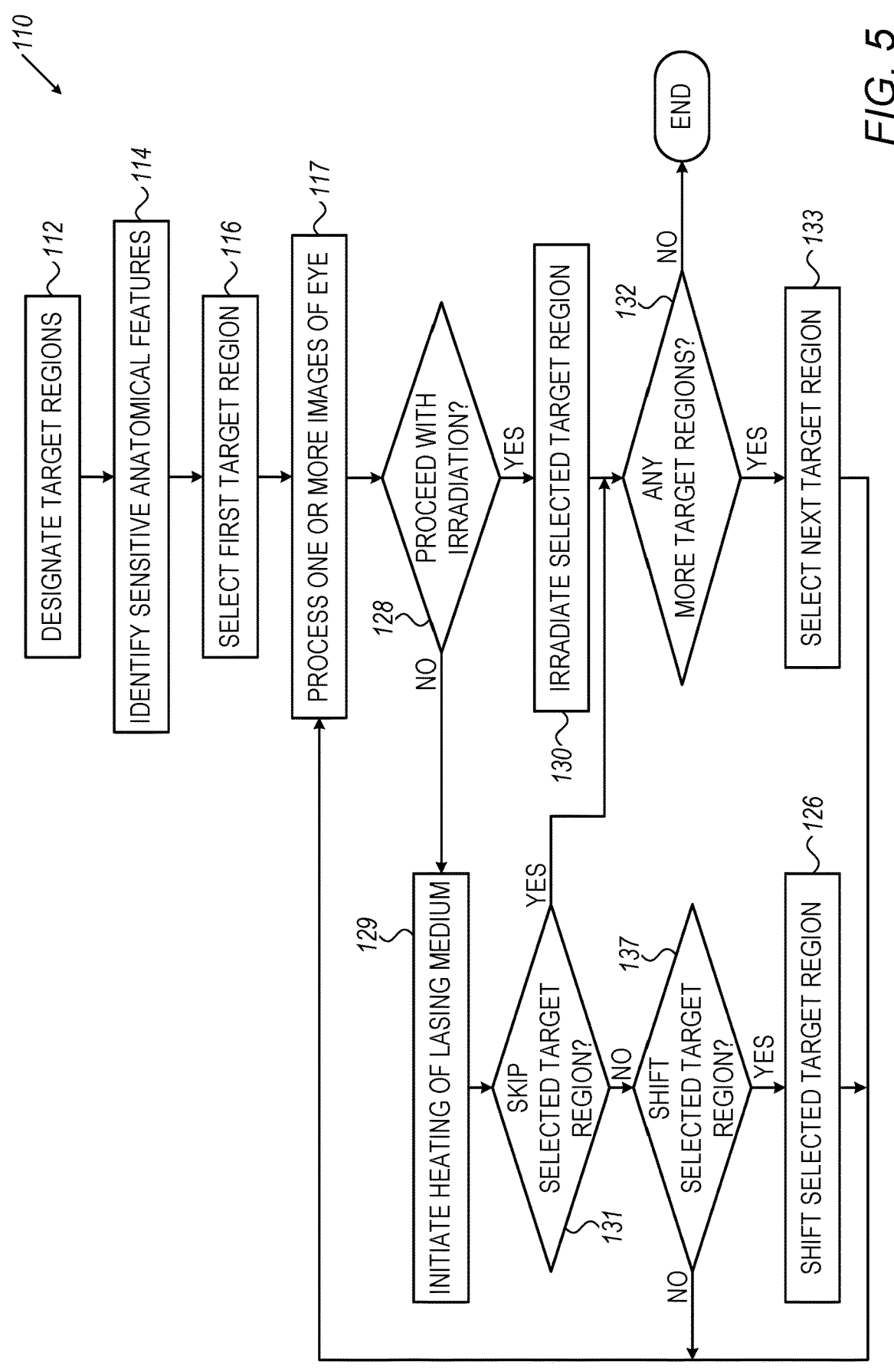
FIG. 5 is a flow diagram for an algorithm for performing an automated trabeculoplasty procedure, in accordance with some embodiments of the present invention.

Reference is now made to FIG. 5, which is a flow diagram for an algorithm 110 for performing an automated trabeculoplasty procedure, in accordance with some embodiments of the present invention.

Algorithm 110 begins with a target-region-designating step 112, at which the controller designates, for irradiation with respective amounts of energy, multiple target regions on the eye of the patient. The respective amounts of energy may be the same; alternatively, one or more amounts of energy may differ from the others.

For example, the controller may define the target regions as described above with reference to FIGS. 3-4. Subsequently, in response to the user's approval of the target regions (as described above with reference to FIG. 3), the controller may designate the target regions for irradiation.

Alternatively, the target regions may be designated using any other technique. For example, as described with reference to FIG. 3 of US Patent Application Publication 2021/0267800, whose disclosure is incorporated herein by reference, the user may specify the locations of the target regions relative to any suitable reference portion of the eye, such as the limbus. As a specific example, the user may specify an elliptical path of target regions adjacent to the limbus, by specifying the number of target regions and the distance from the limbus at which the center or edge of each of the target regions is to be located. In response to this input, the controller may calculate the location of each of the target regions, and, following approval by the user, designate these regions for irradiation.

In some embodiments, subsequently to designating the target regions, the controller, at an anatomical-feature-identifying step 114, searches at least a portion of the eye for any anatomical features that are likely to possess a heightened sensitivity to radiation. Such anatomical features may include, for example, blood vessels, in the event that the blood vessels were not already identified, e.g., during blood-vessel-identifying step 90 of algorithm 88 (FIG. 4). Alternatively or additionally, such anatomical features may include highly pigmented limbal areas, areas affected by trachoma, a local pemphigoid, a local scleritis, a local burn or another injury, or a growth (e.g., a pterygium, a corneal pannus, an arcus senilis, a dermoid or any other type of limbal tumor, or a limbal pinguecula). Any suitable image-processing techniques, such as those described above with reference to blood-vessel-identifying step 90, may be used to identify the sensitive anatomical features.

In some embodiments, the search for sensitive anatomical features is confined to within a predefined distance (e.g., 1.5, 3, or 5 mm) from treatment path 82 (FIG. 3) or the limbus. In other embodiments, the entire eye is searched.

Next, the controller selects the first target region at a target-region-selecting step 116. The controller then begins an iterative treatment process. Each iteration begins with an image-processing step 117, at which the controller processes one or more images of the eye. (As described in US Patent Application Publication 2021/0267800, whose disclosure is incorporated herein by reference, the controller may flash light at the eye while one or more of the images are acquired.) In this regard, reference is now additionally made to FIG. 6A, which is a flow diagram for image-processing step 117, in accordance with some embodiments of the present invention.

In some embodiments, image-processing step 117 begins with an image-acquiring step 118, at which an image of the eye is acquired using camera 54 (FIG. 2).

Subsequently, at a reference-point-identifying step 119, the controller attempts to locate reference point 74 (FIG. 3) in the image. Provided the reference point is located, the controller, at a location-calculating step 120, calculates the location of the selected target region based on the location of the reference point. For example, if the target region was defined to be at a displacement of (dx, dy) from the reference point and, per the image, the reference point is at (x0, y0), the controller may calculate the location of the target region as (x0+dx, y0+dy). (The controller thus compensates for any movement of the eye subsequent to target-region-designating step 112.) If, on the other hand, the reference point cannot be located, the controller proceeds immediately to a deciding step 128, described below.

Following location-calculating step 120, the controller, at an aiming-initiating step 125, initiates the aiming of treatment laser 43 (FIG. 2) at the selected target region, i.e., at the location calculated at location-calculating step 120, by communicating appropriate control signals 39 to aiming motors 61 (FIG. 2). Subsequently, while the laser is being aimed, the controller, at another checking step 122, checks whether there is any static or dynamic obstruction at the location of the target region. A static obstruction, whose position relative to the eye is constant, may include, for example, a growth, such as any of the example growths listed above, or a blood vessel on the sclera, limbus, or cornea (e.g., due to corneal neovascularization). A dynamic obstruction, whose position relative to the eye may change during the procedure, may include, for example, an eyelid, eyelashes, a finger, or a speculum.

More generally, in the context of the present application, including the claims, an "obstruction" may be anything other than tissue that is deemed irradiatable by the user of the system. Thus, the scope of the term "obstruction" may vary between procedures. For example, whereas in some procedures a blood vessel may constitute an obstruction, in other procedures irradiation of a blood vessel may be acceptable or even desired, such that a blood vessel is not an obstruction.

In general, obstructions may be identified using any suitable image-processing techniques, optionally in combination with input from the user. For example, prior to the treatment procedure, the user may indicate one or more portions of the eye that constitute potential obstructions, e.g., by identifying these portions in image 70 (FIG. 3). Subsequently, at checking step 122, the controller may use template matching, edge detection, or any other suitable techniques—including, for example, identifying changes between successive images—to identify the selected portions of the eye. Such techniques may also be used to identify other static or dynamic obstructions that were not necessarily identified in advance by the user.

In some embodiments, the controller, at checking step 122, additionally checks for any obstruction that satisfies one or more predefined criteria, even if the obstruction does not obstruct the selected target region. For example, the controller may check for any obstruction whose size exceeds a predefined threshold or that is moving toward the selected target region.

If an obstruction is identified, the controller proceeds immediately to deciding step 128, at which the controller may decide to refrain from causing the radiation source to irradiate the target region. Otherwise, the controller checks, at another checking step 124, whether the selected target region is too sensitive for irradiation with the amount of energy designated for the target region, as described below with reference to FIG. 7. If the selected target region is too sensitive, the controller proceeds immediately to deciding step 128. Otherwise, the controller, at another checking step 127, checks whether the laser is aimed properly, i.e., whether the laser is aimed at the location of the target region. For example, the controller may process feedback signals 37 from encoders 67 (FIG. 2).

If the laser is improperly aimed, the controller proceeds immediately to deciding step 128. Otherwise, the controller, in some embodiments, performs one or more final verifications at a verifying step 135. (Any of these verifications may alternatively be performed at an earlier stage of image-processing step 117.) For example, as described in US Patent Application Publication 2021/0267800, whose disclosure is incorporated herein by reference, the controller may verify that the target region does not lie (even partly) in a predefined "forbidden zone," which is a static region in the field of view (FOV) of the camera in which, for safety, irradiation is forbidden. Alternatively or additionally, as further described in US Patent Application Publication 2021/0267800, the controller may verify that the target region is within a predefined distance from a previous target region, indicating that the eye is relatively still. Subsequently to performing verifying step 135, the controller performs deciding step 128.

At deciding step 128, the controller decides, in response to processing the images of the eye at image-processing step 117, whether to irradiate the selected target region. The controller may decide to irradiate the selected target region if, for example, the reference point was locatable, no obstruction was identified, the selected target region is not too sensitive, the laser is properly aimed, and verifying step 135 was successfully performed.

Following a decision to irradiate, the target region is irradiated with a treatment beam at an irradiating step 130. Subsequently, the controller checks, at another checking step 132, whether any more target regions have yet to be selected. If yes, the controller selects the next target region at another target-region-selecting step 133, and then begins the next iteration of the treatment by returning to image-processing step 117. Otherwise, the treatment process ends.

If, on the other hand, the controller decides not to irradiate the selected region, the controller, at a heating-initiating step 129, initiates the heating of lasing medium 45, e.g., by communicating appropriate control signals 55 to driver 53 (FIG. 2). (As further described below with reference to FIG. 9, the lasing medium does not lase in response to the heating.) Subsequently, while the lasing medium is heated, the controller decides, at another deciding step 131, whether to skip the selected target region, i.e., refrain from irradiating the selected target region even in a subsequent iteration. The controller may decide to skip the selected target region if, for example, an obstruction was identified at the location of the target region or the target region is too sensitive.

If the controller decides to skip the target region, the controller proceeds to checking step 132. Otherwise, the controller, at another deciding step 137, decides whether to shift the selected target region. The controller may decide to shift the selected target region if, for example, an obstruction was identified at the location of the target region or if the current location of the target region is too sensitive for irradiation.

If the controller decides to shift the target region (e.g., so as to avoid an identified obstruction), the controller shifts the target region at a target-region-shifting step 126. (Typically, the target region is shifted away from the pupil, rather than toward the pupil.) Subsequently, the controller returns to image-processing step 117. Thus, the controller may cause the radiation source to irradiate another location, instead of the original location of the target region, during the subsequent iteration.

If, on the other hand, the controller decides not to shift the target region, the controller returns immediately to image-processing step 117. Thus, the original location of the target region may be irradiated during the subsequent iteration.

In other embodiments, if an obstruction is identified or the target region is too sensitive for irradiation with the designated amount of energy, the controller may decide (after performing aiming-initiating step 125, checking step 127, and verifying step 135) to irradiate the target region with an amount of energy that is less than the designated amount of energy. To control the energy of treatment beams 52, the controller may control the amount of energy pumped to lasing medium 45 (FIG. 2).

Alternatively, in the event that an obstruction is identified or the target region is too sensitive, the controller may terminate the treatment procedure entirely.

In some embodiments, for greater efficiency, calculating step 120 and aiming-initiating step 125 are performed prior to reference-point-identifying step 119, based on the location of the reference point during the previous iteration. In such embodiments, the controller, subsequently to identifying the location of the reference point, checks that the reference point has not moved by more than a predetermined threshold amount. Provided that the reference point has not moved by more than the threshold amount, the controller performs the subsequent steps of image-processing step 117.

Reference is now made to FIG. 6B, which is a flow diagram for image-processing step 117 in accordance with other embodiments of the present invention.

As described above with reference to FIG. 2, in some embodiments, optical unit 30 comprises an aiming laser. In such embodiments, following the aiming of both lasers at the calculated location of the target region, the controller causes the aiming laser to emit an aiming beam. The controller then processes an image of the eye so as to identify the location of the aiming beam on the eye, and calculates the displacement between this location and the calculated location of the target region. The controller may then ascertain that the treatment laser is improperly aimed based on the displacement. For example, the controller may ascertain that the treatment laser is improperly aimed in response to the displacement exceeding a predefined threshold.

For example, as shown in FIG. 6B, in some embodiments, subsequently to calculating the location of the selected target region at calculating step 120, the controller, at another aiming-initiating step 162, initiates the aiming of the aiming laser and treatment laser at the calculated location of the selected target region. (As assumed in FIG. 6B, the calculation may be based on the location of the reference point during the previous iteration.) Subsequently to the aiming of the lasers, the controller, at an emitting step 164, causes the aiming laser to emit an aiming beam. (Alternatively, the aiming beam may be continuously emitted during the procedure.) In some embodiments, the wavelength of the aiming beam is greater than 700 nm (i.e., the aiming beam is infrared) such that the aiming beam is invisible to, and thus does not disturb, the patient.

Next, the controller acquires at least one image of the eye. For example, as assumed in FIG. 6B, the controller may, while the aiming beam is emitted, acquire a single image including a first frame, in which the aiming beam appears, and a second frame, in which the aiming beam does not appear. For example, camera 54 (FIG. 2) may comprise a filter matrix (or "filter array") configured to filter the aiming beam from the second frame. For example, for embodiments in which the wavelength of the aiming beam is greater than 700 nm, the filter matrix may filter out wavelengths greater than 700 nm. Alternatively, the wavelength of the aiming beam may be selected such that a standard Bayer filter filters out the aiming beam from the second frame. For example, the aiming beam may be red, such that the aiming beam is visible in the first (red) frame of the image but not the second (green) frame of the image.

Subsequently, at an aiming-beam-locating step 166, the controller attempts to locate the aiming beam in the first frame of the image. If the aiming beam cannot be located, the controller proceeds immediately to deciding step 128. Otherwise, the controller, at a reference-point-locating step 168, attempts to locate the reference point in the second frame of the image. If the reference point cannot be located, the controller proceeds immediately to deciding step 128. Otherwise, the controller proceeds to checking step 127, at which the controller checks whether (i) the aiming beam impinges on the calculated location of the target region, and (ii) the displacement between the current location of the reference point and the location of the reference point during the previous iteration is less than a predefined threshold. If not, the controller proceeds immediately to deciding step 128. Otherwise, the controller performs checking step 122, checking step 124, and verifying step 135.

In other embodiments, the controller acquires two images of the eye: a first image, which is acquired while the aiming beam is emitted such that the aiming beam appears in the first image (as described above), and a second image, which is acquired before or after the aiming beam is emitted such that the aiming beam does not appear in the second image. For example, after acquiring the first image, the controller may turn the aiming beam off, and then acquire the second image. The controller may then, at aiming-beam-locating step 166, attempt to locate the aiming beam in the first image, and, at reference-point-locating step 168, attempt to locate the reference point in the second image.

In yet other embodiments, the controller acquires a single image, and locates the aiming beam and reference point in the same frame(s) of the image.

Figure 7:
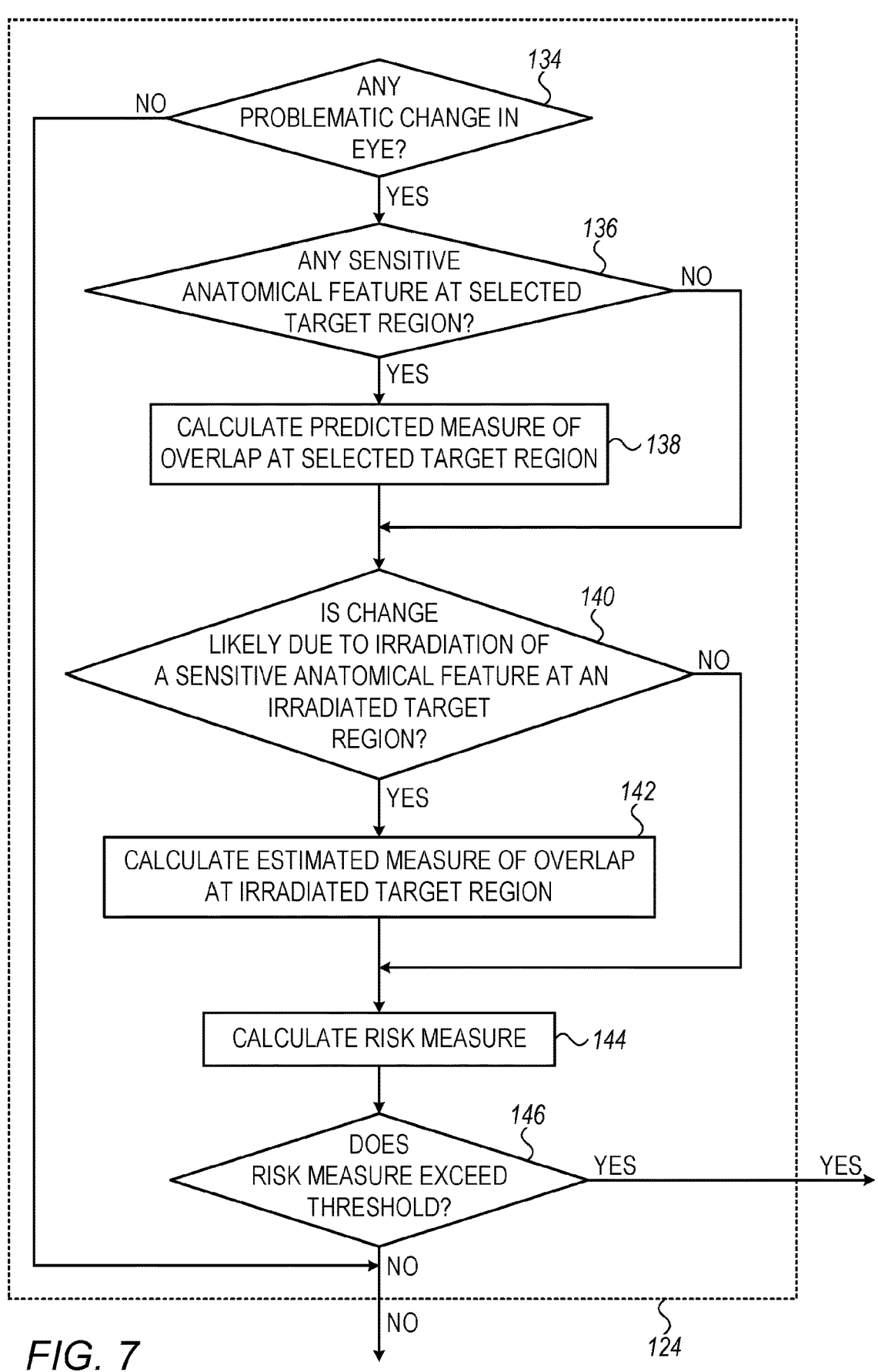
FIG. 7 is a flow diagram for a checking step, in accordance with some embodiments of the present invention.

Reference is now made to FIG. 7, which is a flow diagram for checking step 124, in accordance with some embodiments of the present invention.

Checking step 124 begins with a first assessing step 134, at which the controller processes the latest acquired image, typically together with previously acquired images, so as to ascertain whether a problematic change—such as bleeding, swelling, a change in the density of identifiable blood vessels, the formation of one or more bubbles, and/or a change in color—has occurred in the eye. If no such change is identified, the controller decides that the selected target region is not too sensitive for irradiation. Otherwise, the controller may decide that the selected target region is too sensitive for irradiation, as further described below.

In performing first assessing step 134, the controller may use any suitable image-processing techniques, including, for example, optical flow, pattern recognition, edge detection, segmentation, differential checks, and/or color monitoring. For example, the controller may align the latest image with a previously acquired image (such as an image acquired prior to the treatment procedure), using pattern recognition to facilitate the alignment. Subsequently, the controller may subtract the previously acquired image from the current image, and then use edge detection or segmentation to identify the locations of any features of interest—such as a change in color or other features indicating bleeding or swelling—in the difference image.

In response to identifying a problematic change, the controller ascertains, at a second assessing step 136, whether any sensitive anatomical feature (identified at anatomical-feature-identifying step 114 of FIG. 5) is located at the selected target region. In the context of the present application, including the claims, an anatomical feature is said to be located at a target region if any portion of the anatomical feature is within a predefined threshold distance of the target region. The threshold distance is typically defined automatically or semi-automatically, based on (i) the maximum possible movement of the eye between image-acquiring step 118 (FIGS. 6A-B) and irradiating step 130 (FIG. 5), and (ii) the calibration precision of the laser. In some embodiments, the predefined threshold distance is less than 3 mm.

In response to a sensitive anatomical feature being located at the selected target region, the controller, at an overlap-predicting step 138, calculates a predicted measure of overlap between a treatment beam irradiating the selected target region and the anatomical feature. The predicted measure of overlap may be expressed, for example, as an amount of area of the anatomical feature that the beam is predicted to overlap.

In calculating the predicted measure of overlap, the controller may assume that the treatment beam does not deviate from the target region. Alternatively, prior to the procedure, the controller may calculate a probability distribution for the deviation of the treatment beam from the target region, and/or one or more statistics of this distribution such as a maximum, mean, or median deviation. Subsequently, the controller may calculate the predicted measure of overlap based on the statistics, e.g., by assuming that the treatment beam deviates toward the anatomical feature by the maximum, mean, or median deviation.

Subsequently, or if no sensitive anatomical feature is present at the selected target region, the controller ascertains, at a third assessing step 140, whether the change identified at first assessing step 134 is likely due to the irradiation of a sensitive anatomical feature at any one of the irradiated target regions. For example, the controller may check whether any portion of the image showing the change is within a predefined threshold distance of such a sensitive anatomical feature.

If the change is likely due to the irradiation of a sensitive anatomical feature, the controller, at an overlap-estimating step 142, calculates an estimated measure of overlap between the treatment beam that irradiated the target region and the anatomical feature. The estimated measure of overlap may be expressed, for example, as an amount of area of the anatomical feature that the beam is estimated to have overlapped. Subsequently to calculating the estimated measure of overlap, or if the change was likely not due to the irradiation of a sensitive anatomical feature, the controller performs risk-measure-calculating step 144, described below.

In some embodiments, the controller bases the estimate of the measure of overlap on the location of the aiming beam as identified at aiming-beam-locating step 166 (FIG. 6B). For example, the controller may assume the treatment beam impinged on (i) the position of the aiming beam in the image acquired immediately before the firing of the treatment beam, or (ii) the position of the aiming beam in the image acquired immediately after the firing of the treatment beam. Alternatively, the controller may compute the average of (i) and (ii), and assume the treatment beam impinged on the eye at this average position.

Alternatively, for embodiments in which an aiming beam is not fired, the controller may estimate the measure of overlap based on the location at which the treatment laser was aimed (as indicated by the feedback signal from the encoders) along with an estimated spot size of the treatment beam on the eye.

In addition to estimating and predicting measures of overlap, the controller may calculate an estimated amount of energy delivered (by the treatment beam) to the sensitive anatomical feature at the irradiated target region, along with a predicted amount of energy that will be delivered (by the treatment beam) to the sensitive anatomical feature at the selected target region. Typically, the estimated or predicted amount of delivered energy is a function of the estimated or predicted measure of overlap (respectively), along with parameters that vary with the setup of system 20 (FIG. 1), such as the energy and spot size of the treatment beam.

At risk-measure-calculating step 144, the controller calculates a risk measure associated with irradiating the selected target region. Typically, the risk measure is greater if a sensitive anatomical feature is at the selected target region, relative to if no sensitive anatomical feature is at the selected target region. Moreover, the risk measure is an increasing function of the predicted quantity for the selected target region, given that a higher measure of overlap or amount of delivered energy is more likely to cause another change in the eye. Conversely, typically, the risk measure is greater if the identified change was likely not due to the irradiation of a sensitive anatomical feature, and is a decreasing function of the estimated quantity. Thus, for example, the risk measure may be an increasing function of the ratio of the predicted quantity to the estimated quantity.

Alternatively or additionally, the risk measure may be based on the medical profile of the patient, particularly those aspects of the medical profile related to the sensitivity of the patient's eyes. For example, the risk measure may be based on parameters such as the patient's age, sex, medication history (particularly with regards to use of topical eye medications), frequency of contact lens use, and/or intraocular pressure. Thus, for example, a higher risk measure may be calculated for a patient with a history of topical eye medication use, relative to another patient without such a history.

Alternatively or additionally, the risk measure may be based on the type of anatomical feature at the selected target region. For example, a larger blood vessel may be known, a priori, to have a greater chance of bleeding than a smaller blood vessel; consequently, the risk measure be higher for the former than for the latter.

Alternatively or additionally, the risk measure may be an increasing function of the similarity between the anatomical feature at the selected target region and the irradiated anatomical feature identified at third assessing step 140. The similarity may include, for example, similarity in type, color, and/or size.

Alternatively or additionally, the risk measure may be based on the type of identified change; for example, the risk measure may be higher in response to detecting bleeding or swelling, relative to detecting a mere change in color.

Subsequently to calculating the risk measure, the controller, at a fourth assessing step 146, compares the risk measure to a predefined threshold. If the risk measure exceeds the threshold, the controller decides that the selected target region is too sensitive for irradiation. In response thereto, the controller may refrain from irradiating the target region, or at least lower the energy with which the target region is irradiated, as described above with reference to FIG. 5.

In the event that one or more identified changes are likely to have been caused by the irradiation of multiple sensitive anatomical features, the controller considers each of these anatomical features when evaluating the risk for the selected target region. For example, the risk measure may be based on the respective types of the sensitive anatomical features, and/or the respective estimated measures of overlap for the sensitive anatomical features.

It is noted that the flow diagram of FIG. 7 is presented by way of example only, and that many other embodiments of checking step 124 are included within the scope of the present invention. For example:

(i) Alternatively or additionally to ascertaining whether there is a sensitive anatomical feature at the selected target region, the controller may ascertain whether the selected target region is within a predefined threshold distance of a sensitive region of the eye, such as the pupil or an agglomeration of blood vessels. If yes, the risk measure may be increased, optionally as a function of the distance between the target region and the sensitive region.

(ii) In response to identifying a problematic change, the controller may acquire and process additional images, prior to proceeding with the remainder of checking step 124. The processing of the additional images may allow the controller to verify the change, identify the type of change, and/or monitor the change for safety purposes. Thus, for example, the treatment procedure may be terminated if bleeding does not stop within a predefined duration of time or if the area covered by blood exceeds a predefined threshold.

(iii) The controller may decide that the selected target region is too sensitive for irradiation, even without calculating a risk measure. For example, such a decision may be made immediately following an ascertainment of the presence of a sensitive anatomical feature at second assessing step 136. Alternatively, such a decision may be made in response to the predicted measure of overlap, or the predicted amount of delivered energy, exceeding a predefined threshold, which may be an absolute number or a number derived from the corresponding estimate for an irradiated target region identified at third assessing step 140. Alternatively, such a decision may be made in response to the sensitive anatomical feature at the selected target region and the irradiated anatomical feature being of the same type.

Figure 8:
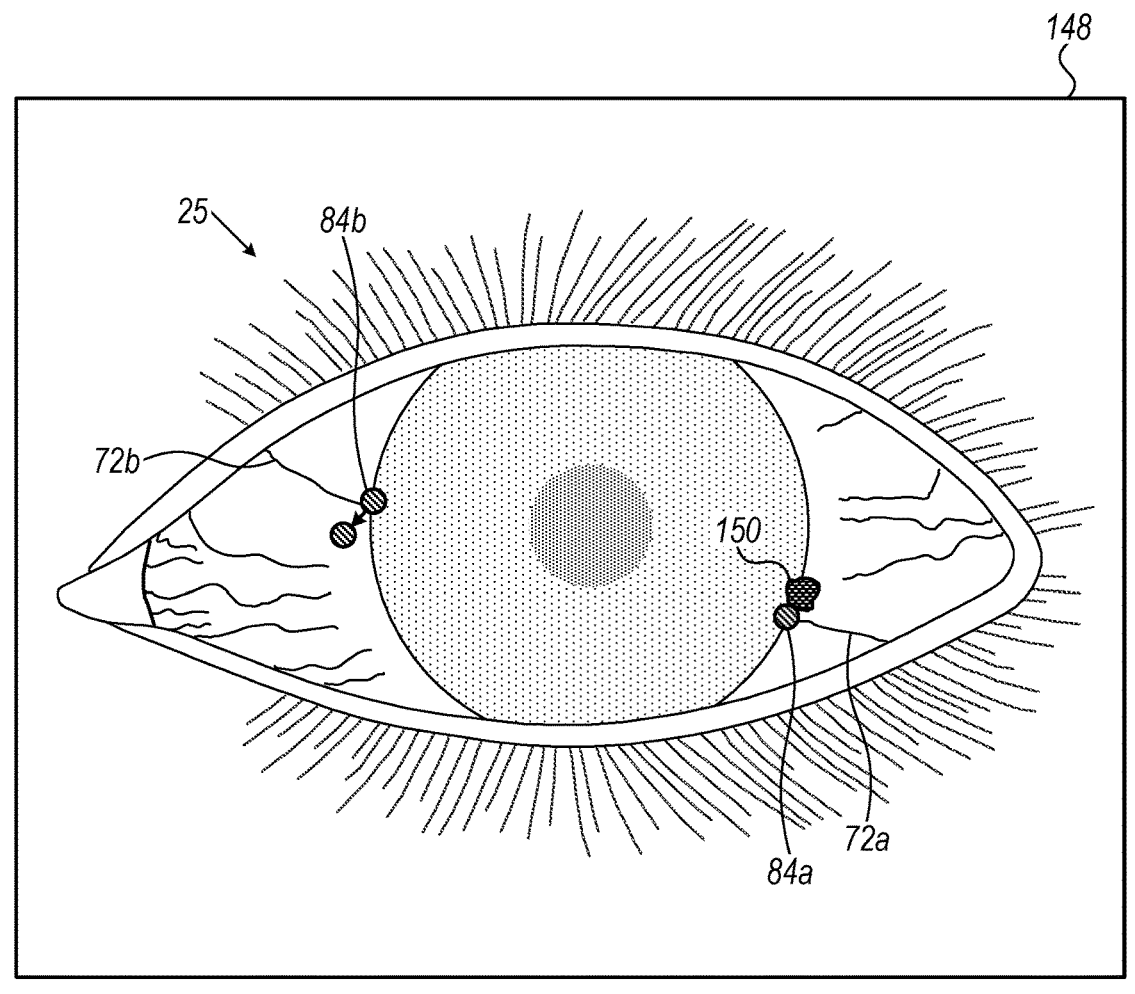
FIG. 8 pictorially illustrates an example performance of a checking step and a target-region-shifting step, in accordance with some embodiments of the present invention.

Reference is now made to FIG. 8, which pictorially illustrates an example performance of checking step 124 (FIGS. 6A-B) and target-region-shifting step 126 (FIG. 5), in accordance with some embodiments of the present invention.

Figure 6A:
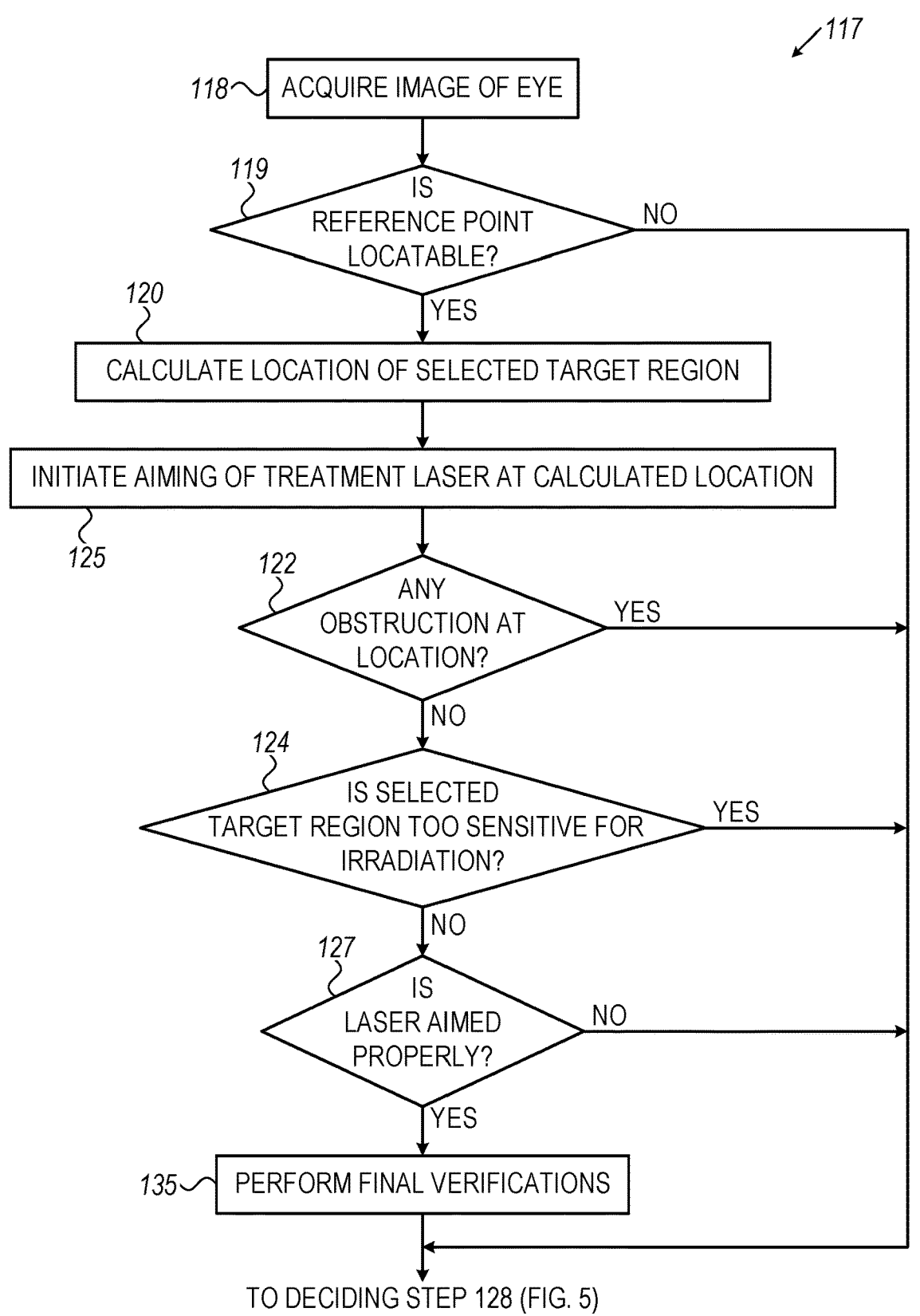

FIG. 8 shows an image 148 of eye 25, which is acquired at image-acquiring step 118 (FIGS. 6A-B). By processing image 148 as described above with reference to first assessing step 134 (FIG. 7) of checking step 124, the controller may identify a blood pool 150 near an irradiated target region 84*a*. Blood pool 150 indicates that the irradiation of target region 84*a* likely caused a first blood vessel 72*a*, which is located at target region 84*a*, to bleed. Hence, prior to irradiating another target region 84*b*, the controller may shift target region 84*b* away from a second blood vessel 72*b*, thus reducing the likelihood of another bleeding incident.

Heating Pulses

Figure 9:
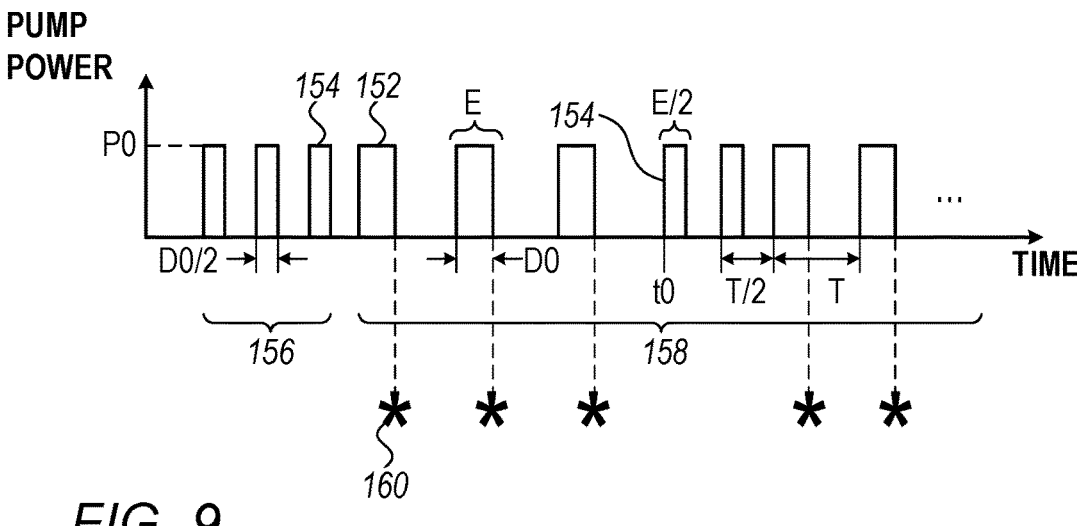
FIG. 9 is a schematic illustration of a timeline of lasing-causing pulses and heating pulses, in accordance with some embodiments of the present invention.

Reference is again made to FIG. 2, and is also made to FIG. 9, which is a schematic illustration of a timeline of lasing-causing pulses 152 and heating pulses 154, in accordance with some embodiments of the present invention.

Typically, prior to starting the irradiation of the target regions (per algorithm 110 of FIG. 5, for example), controller 44 (e.g., by controlling driver 53) causes pump source 47 to heat lasing medium 45 without causing the lasing medium to lase. For example, the controller may cause the pump source to pump the lasing medium with a train 156 of one or more heating pulses 154, which are further described below. As a result of this heating, the lasing medium may reach thermal equilibrium before emitting any treatment beams.

To start the irradiation of the target regions, the controller (e.g., by controlling driver 53) drives the pump source to begin pumping lasing medium 45 with a train 158 of lasing-causing pulses 152. Typically, train 158 is periodic with a period T, i.e., each lasing-causing pulse 152 (aside from any lasing-causing pulse that follows a heating pulse 154) occurs at an interval of T from the preceding lasing-causing pulse. Each lasing-causing pulse 152 causes the lasing medium to lase, and thus emit a treatment beam 52, close to the end of the pulse, as indicated in FIG. 9 by a lasing-marker 160. (Irradiating step 130 of FIG. 5 includes the pumping of the lasing medium with a lasing-causing pulse and the emission of a treatment beam.)

Subsequently to starting the irradiation of the target regions, the controller may cause the pump source to substitute one or more heating pulses 154 for one of the lasing-causing pulses. Each heating pulse 154 is configured to heat the lasing medium without causing the lasing medium to lase.

For example, as described above with reference to FIG. 5 and FIGS. 6A-B, the controller may process one or more images of the eye acquired by camera 54 (e.g., at image-acquiring step 118), and cause the pump source to substitute the heating pulses in response to processing the images. For example, the controller may cause the pump source to substitute the heating pulses in response to identifying (at checking step 122) an obstruction of the eye, identifying (at checking step 124) a change in the eye, or ascertaining (at checking step 127) that the treatment laser is not aimed at the location of the target region that is to be irradiated. Alternatively, the controller may cause the pump source to substitute the heating pulses in response to a signal indicating an error. For example, feedback signal 37 (FIG. 2) may indicate that the beam-directing elements are not oriented as expected, or another signal may indicate a fault in the treatment laser or in any other component of the optical unit.

Typically, the total energy E2 of the heating pulses that substitute for a lasing-causing pulse is approximately equal to the energy E0 of the lasing-causing pulse minus the energy E1 lost by the lasing medium during lasing. Thus, the thermal equilibrium of the lasing medium is maintained.

Typically, E1 is between 0 and 30% of E0, such that E2 is between 70% and 100% of E0.

For example, the pump source may substitute a single heating pulse that spreads the energy E2 over a sufficiently large duration such that the lasing threshold of the lasing medium is not reached.

Alternatively, the pump source may substitute N>1 heating pulses. For example, supposing the duration of each lasing-causing pulse is DO (where DO is between 120 and 150 microseconds, for example), each of the heating pulses may have a duration DO but a lower average power than that of each lasing-causing pulse, such that the energy of the heating pulse is E2/N. Alternatively, each of the heating pulses may have a duration of D0/N. For example, each heating pulse may have a duration of D0/N and a peak power equal to that of each of the lasing-causing pulses. As a specific example, supposing that the instantaneous power of each lasing-causing pulse is approximately constant at P0=E0/D0, each heating pulse may have a duration D0/N with an instantaneous power approximately constant at P0, as shown in FIG. 9 for N=2.

Typically, the heating pulses are substituted at times $\{k*T/N\}$, $k=0 \ldots N-1$ from the time t0 at which the lasing-causing pulse was to have been pumped. For example, as shown in FIG. 9 for N=2, the first heating pulse may begin at t0, and the second may begin at t0+T/2.

Although the above description pertains mainly to trabeculoplasty procedures, it is noted that embodiments of the present invention may be applied to any type of procedure in which target regions of the eye are irradiated, such as a transscleral cyclophotocoagulation (TSCPC) or tissue shrinkage procedure.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a laser, comprising a pump source and a lasing medium; and
   a controller, configured to:
     designate multiple target regions on an eye of a patient for irradiation, in sequence, by the laser,
     start the irradiation of the target regions, by driving the pump source to begin pumping the lasing medium with a train of lasing-causing pulses, each of which is configured to cause the lasing medium to lase, and
     subsequently to starting the irradiation of the target regions, cause the pump source to substitute one or more heating pulses for one of the lasing-causing pulses, the heating pulses being configured to heat the lasing medium without causing the lasing medium to lase.

2. The system according to claim 1, wherein the controller is further configured to cause the pump source, prior to starting the irradiation of the target regions, to heat the lasing medium without causing the lasing medium to lase.

3. The system according to claim 1, wherein a total energy of the heating pulses is between 70% and 100% of a lasing-causing-pulse energy of each of the lasing-causing pulses.

4. The system according to claim 1, wherein the one or more heating pulses consist of N>1 heating pulses.

5. The system according to claim 4, wherein each of the heating pulses has a heating-pulse duration of D0/N, D0 being a lasing-causing-pulse duration of each of the lasing-causing pulses.

6. The system according to claim 5, wherein each of the heating pulses has a peak power equal to that of each of the lasing-causing pulses.

7. The system according to claim 4, wherein the train is periodic with a period T, and wherein the controller is configured to cause the pump source to substitute the heating pulses at times {k*T/N}, k=0 . . . N−1 from a time at which the one of the lasing-causing pulses was to have been pumped.

8. The system according to claim 1, wherein the controller is configured to cause the pump source to substitute the heating pulses in response to a signal indicating an error.

9. The system according to claim 1, wherein the controller is further configured to process one or more images of the eye acquired by a camera, and wherein the controller is configured to cause the pump source to substitute the heating pulses in response to processing the images.

10. The system according to claim 9, wherein the controller is configured to identify an obstruction of the eye by processing the images, and wherein the controller is configured to cause the pump source to substitute the heating pulses in response to identifying the obstruction.

11. The system according to claim 9, wherein the controller is configured to identify a change in the eye by processing the images, and wherein the controller is configured to cause the pump source to substitute the heating pulses in response to identifying the change.

12. The system according to claim 11, wherein the change includes a formation of one or more bubbles.

13. The system according to claim 9,
wherein the controller is configured to identify a reference-point location of a reference point on the eye by processing the images,
wherein the controller is further configured to:
 based on the reference-point location, calculate a target-region location of one of the target regions, and ascertain that the laser is not aimed at the target-region location, and
wherein the controller is configured to cause the pump source to substitute the heating pulses in response to the ascertaining.

14. The system according to claim 13, further comprising one or more motors, wherein the controller is further configured to aim the laser using the motors, and wherein the controller is configured to ascertain that the laser is not aimed at the target-region location in response to respective signals from respective encoders of the motors.

15. The system according to claim 13,
wherein the laser is a treatment laser,
wherein the system further comprises an aiming laser,
wherein the controller is further configured to:
 cause the aiming laser to emit an aiming beam at a location at which the treatment laser is aimed, and identify an aiming-beam location of the aiming beam by processing the images, and wherein the controller is configured to ascertain that the treatment laser is not aimed at the target-region location based on a displacement between the aiming-beam location and the target-region location.

16. The system according to claim 15, wherein a wavelength of the aiming beam is greater than 700 nm.

17. The system according to claim 15,
wherein the images include a first image, which is acquired while the aiming beam is emitted such that the aiming beam appears in the first image, and a second image, which is acquired before or after the aiming beam is emitted such that the aiming beam does not appear in the second image,
wherein the controller is configured to identify the aiming-beam location in the first image, and
wherein the controller is configured to identify the reference-point location in the second image.

18. The system according to claim 15,
wherein the images consist of a single image including a first frame, in which the aiming beam appears, and a second frame, in which the aiming beam does not appear,
wherein the controller is configured to identify the aiming-beam location in the first frame, and
wherein the controller is configured to identify the reference-point location in the second frame.

19. A method, comprising:
designating multiple target regions on an eye of a patient for irradiation, in sequence, by a laser;
starting the irradiation of the target regions, by driving a pump source to begin pumping a lasing medium of the laser with a train of lasing-causing pulses, each of which is configured to cause the lasing medium to lase; and
subsequently to starting the irradiation of the target regions, causing the pump source to substitute one or more heating pulses for one of the lasing-causing pulses, the heating pulses being configured to heat the lasing medium without causing the lasing medium to lase.

20. The method according to claim 19, further comprising, prior to starting the irradiation of the target regions, causing the pump source to heat the lasing medium without causing the lasing medium to lase.

21. The method according to claim 19, wherein a total energy of the heating pulses is between 70% and 100% of a lasing-causing-pulse energy of each of the lasing-causing pulses.

22. The method according to claim 19, wherein the one or more heating pulses consist of N>1 heating pulses.

23. The method according to claim 22, wherein each of the heating pulses has a heating-pulse duration of D0/N, D0 being a lasing-causing-pulse duration of each of the lasing-causing pulses.

24. The method according to claim 23, wherein each of the heating pulses has a peak power equal to that of each of the lasing-causing pulses.

25. The method according to claim 22, wherein the train is periodic with a period T, and wherein causing the pump source to substitute the heating pulses comprises causing the pump source to substitute the heating pulses at times {k*T/N}, k=0 . . . N−1 from a time at which the one of the lasing-causing pulses was to have been pumped.

26. The method according to claim 19, wherein causing the pump source to substitute the heating pulses comprises causing the pump source to substitute the heating pulses in response to a signal indicating an error.

27. The method according to claim 19, further comprising processing one or more images of the eye acquired by a camera, wherein causing the pump source to substitute the heating pulses comprises causing the pump source to substitute the heating pulses in response to processing the images.

28. The method according to claim 27, wherein processing the images comprises identifying an obstruction of the eye, and wherein causing the pump source to substitute the heating pulses comprises causing the pump source to substitute the heating pulses in response to identifying the obstruction.

29. The method according to claim 27, wherein processing the images comprises identifying a change in the eye, and wherein causing the pump source to substitute the heating pulses comprises causing the pump source to substitute the heating pulses in response to identifying the change.

30. The method according to claim 29, wherein the change includes a formation of one or more bubbles.

31. The method according to claim 27,
wherein processing the images comprises identifying a reference-point location of a reference point on the eye,
wherein the method further comprises:
based on the reference-point location, calculating a target-region location of one of the target regions; and
ascertaining that the laser is not aimed at the target-region location, and
wherein causing the pump source to substitute the heating pulses comprises causing the pump source to substitute the heating pulses in response to the ascertaining.

32. The method according to claim 31, wherein the laser is aimed using one or more motors, and wherein ascertaining that the laser is not aimed at the target-region location comprises ascertaining that the laser is not aimed at the target-region location in response to respective signals from respective encoders of the motors.

33. The method according to claim 31,
wherein the laser is a treatment laser,
wherein the method further comprises causing an aiming laser to emit an aiming beam at a location at which the treatment laser is aimed,
wherein processing the images further comprises identifying an aiming-beam location of the aiming beam, and
wherein ascertaining that the treatment laser is not aimed at the target-region location comprises ascertaining that the treatment laser is not aimed at the target-region location based on a displacement between the aiming-beam location and the target-region location.

34. The method according to claim 33, wherein a wavelength of the aiming beam is greater than 700 nm.

35. The method according to claim 33,
wherein the images include a first image, which is acquired while the aiming beam is emitted such that the aiming beam appears in the first image, and a second image, which is acquired before or after the aiming beam is emitted such that the aiming beam does not appear in the second image,
wherein identifying the aiming-beam location comprises identifying the aiming-beam location in the first image, and
wherein identifying the reference-point location comprises identifying the reference-point location in the second image.

36. The method according to claim 33,
wherein the images consist of a single image including a first frame, in which the aiming beam appears, and a second frame, in which the aiming beam does not appear,
wherein identifying the aiming-beam location comprises identifying the aiming-beam location in the first frame, and
wherein identifying the reference-point location comprises identifying the reference-point location in the second frame.

* * * * *